(12) United States Patent (10) Patent No.: US 8,339,586 B2
Zahniser et al. (45) Date of Patent: Dec. 25, 2012

(54) MEASURING VOLUME AND CONSTITUENTS OF CELLS

(75) Inventors: Michael Zahniser, Jamaica Plain, MA (US); Russell Zahniser, Dorchester, MA (US)

(73) Assignee: Constitution Medical, Inc., Boston, MA (US)

( * ) Notice: Subject to any disclaimer, the term of this patent is extended or adjusted under 35 U.S.C. 154(b) by 0 days.

(21) Appl. No.: 13/446,996

(22) Filed: Apr. 13, 2012

(65) Prior Publication Data

US 2012/0262703 A1  Oct. 18, 2012

Related U.S. Application Data

(60) Provisional application No. 61/476,170, filed on Apr. 15, 2011, provisional application No. 61/510,614, filed on Jul. 22, 2011, provisional application No. 61/476,179, filed on Apr. 15, 2011, provisional application No. 61/510,710, filed on Jul. 22, 2011, provisional application No. 61/589,672, filed on Jan. 23, 2012.

(51) Int. Cl.
 G01N 33/48 (2006.01)
 G06K 9/00 (2006.01)
 A61B 5/00 (2006.01)

(52) U.S. Cl. ........... 356/39; 382/133; 382/134; 600/322

(58) Field of Classification Search ........................ None
See application file for complete search history.

(56) References Cited

U.S. PATENT DOCUMENTS

| | | | |
|---|---|---|---|
| 3,770,349 A | 11/1973 | Legorreta-Sanchez | |
| 4,097,845 A | 6/1978 | Bacus | |
| 4,125,828 A | 11/1978 | Resnick et al. | |
| 4,199,748 A | 4/1980 | Bacus | |
| 4,207,554 A | 6/1980 | Resnick et al. | |
| 4,242,730 A * | 12/1980 | Golias et al. | 356/39 |
| 4,453,266 A | 6/1984 | Bacus | |
| 4,741,043 A | 4/1988 | Bacus | |
| 4,998,533 A | 3/1991 | Winkelman | |

(Continued)

FOREIGN PATENT DOCUMENTS

EP  0 794 435  1/2003

(Continued)

OTHER PUBLICATIONS

Bacus, J. et al., "An Automated Method of Differential Red Blood Cell Classification With Application to the Diagnosis of Anemia", *The Journal of Histochemistry and Cytochemistry*, vol. 25:614-32 (1977).

(Continued)

*Primary Examiner* — Gordon Stock, Jr.
(74) *Attorney, Agent, or Firm* — Fish & Richardson P.C.

(57) ABSTRACT

A method of determining a volume of a platelet includes: (a) illuminating the platelet with incident light at a plurality of illumination wavelengths; (b) obtaining at least one two-dimensional image of the platelet corresponding to each illumination wavelength; (c) for each illumination wavelength, determining a mean optical density and a maximum optical density for the platelet; (d) determining an area of the platelet; (e) for each illumination wavelength, determining a volume of the platelet; (f) for each illumination wavelength, determining an integrated optical density for the platelet; and (g) determining the volume of the platelet based on a weighted combination of the area of the platelet, the volumes of the platelet corresponding to each of the illumination wavelengths, and the integrated optical densities for the platelet corresponding to each of the illumination wavelengths.

40 Claims, 6 Drawing Sheets

U.S. PATENT DOCUMENTS

| | | |
|---|---|---|
| 5,127,406 A | 7/1992 | Yamaguchi |
| 5,304,491 A | 4/1994 | Chiang et al. |
| 5,305,076 A | 4/1994 | Inoue et al. |
| 5,351,198 A | 9/1994 | Adachi et al. |
| 5,385,143 A | 1/1995 | Aoyagi |
| 5,548,395 A | 8/1996 | Kosaka |
| 5,720,284 A | 2/1998 | Aoyagi et al. |
| 5,722,398 A | 3/1998 | Ishihara et al. |
| 5,741,213 A | 4/1998 | Kouchi et al. |
| 5,766,125 A | 6/1998 | Aoyagi et al. |
| 5,784,162 A | 7/1998 | Cabib et al. |
| 5,825,477 A | 10/1998 | Furuie |
| 5,882,933 A | 3/1999 | Li et al. |
| 5,882,934 A | 3/1999 | Li et al. |
| 5,891,734 A | 4/1999 | Gill et al. |
| 5,948,686 A | 9/1999 | Wardlaw |
| 5,958,781 A | 9/1999 | Wong et al. |
| 5,968,832 A | 10/1999 | Uchihashi et al. |
| 5,978,497 A * | 11/1999 | Lee et al. ............ 382/133 |
| 6,061,583 A | 5/2000 | Ishihara et al. |
| 6,087,182 A | 7/2000 | Jeng et al. |
| 6,104,939 A | 8/2000 | Groner et al. |
| 6,151,405 A | 11/2000 | Douglass et al. |
| 6,169,816 B1 | 1/2001 | Ravkin |
| 6,200,500 B1 | 3/2001 | Ryan |
| 6,235,536 B1 | 5/2001 | Wardlaw |
| 6,251,615 B1 | 6/2001 | Oberhardt |
| 6,350,613 B1 | 2/2002 | Wardlaw et al. |
| 6,567,678 B1 | 5/2003 | Oosta et al. |
| 6,569,682 B2 | 5/2003 | Elliott et al. |
| RE38,131 E | 6/2003 | Uchihashi et al. |
| 6,593,102 B2 | 7/2003 | Zahniser et al. |
| 6,622,095 B2 | 9/2003 | Kobayashi et al. |
| 6,743,576 B1 | 6/2004 | Sabry et al. |
| 6,746,848 B2 * | 6/2004 | Smith ............ 435/7.23 |
| 6,748,337 B2 | 6/2004 | Wardlaw et al. |
| 6,869,570 B2 | 3/2005 | Wardlaw |
| 6,916,662 B2 | 7/2005 | Kendall et al. |
| 6,930,773 B2 | 8/2005 | Cronin et al. |
| 7,026,110 B1 | 4/2006 | Veriac et al. |
| 7,095,492 B2 | 8/2006 | Kramer |
| 7,257,433 B2 | 8/2007 | Takamura et al. |
| 7,313,426 B2 | 12/2007 | Takeda et al. |
| 7,324,194 B2 | 1/2008 | Roche et al. |
| 7,450,223 B2 | 11/2008 | Ikeuchi et al. |
| 7,482,165 B2 | 1/2009 | Zheng et al. |
| 7,561,329 B2 | 7/2009 | Zahniser et al. |
| 7,633,604 B2 | 12/2009 | Ikeuchi et al. |
| 7,660,449 B2 | 2/2010 | Hays et al. |
| 7,754,487 B2 | 7/2010 | Ortiz et al. |
| 7,782,447 B2 | 8/2010 | Lindberg |
| 7,796,797 B2 | 9/2010 | Nakaya et al. |
| 7,903,241 B2 | 3/2011 | Wardlaw et al. |
| 7,929,121 B2 * | 4/2011 | Wardlaw et al. ............ 356/39 |
| 7,929,122 B2 * | 4/2011 | Wardlaw et al. ............ 356/40 |
| 7,951,599 B2 | 5/2011 | Levine et al. |
| 2002/0081013 A1 | 6/2002 | Raz |
| 2003/0030783 A1 * | 2/2003 | Roche et al. ............ 356/39 |
| 2004/0156037 A1 | 8/2004 | Mawhirt et al. |
| 2005/0019796 A1 | 1/2005 | Meiring et al. |
| 2006/0050947 A1 * | 3/2006 | Petrou et al. ............ 382/133 |
| 2006/0223172 A1 | 10/2006 | Bedingham et al. |
| 2006/0263905 A1 | 11/2006 | Mishima et al. |
| 2007/0054404 A1 | 3/2007 | Huo et al. |
| 2007/0140543 A1 * | 6/2007 | D'Errico et al. ............ 382/133 |
| 2008/0138852 A1 | 6/2008 | Winkelman et al. |
| 2008/0144005 A1 | 6/2008 | Guiney et al. |
| 2009/0130647 A1 | 5/2009 | Nagai et al. |
| 2009/0198168 A1 | 8/2009 | Hiruma et al. |
| 2009/0214096 A1 * | 8/2009 | Andrushkiw et al. ............ 382/131 |
| 2009/0238438 A1 * | 9/2009 | Wardlaw et al. ............ 382/134 |
| 2009/0262993 A1 * | 10/2009 | Kotsianti et al. ............ 382/128 |
| 2009/0269799 A1 | 10/2009 | Winkelman et al. |
| 2010/0041011 A1 | 2/2010 | Van Agthoven et al. |
| 2010/0159605 A1 | 6/2010 | Zhang et al. |
| 2010/0240055 A1 | 9/2010 | Godefroy et al. |
| 2011/0151502 A1 | 6/2011 | Kendall et al. |
| 2011/0164803 A1 | 7/2011 | Wang et al. |
| 2011/0256573 A1 | 10/2011 | Davis et al. |

FOREIGN PATENT DOCUMENTS

| | | |
|---|---|---|
| GB | 2308444 | 6/1997 |
| JP | 2002-516982 | 6/2002 |
| WO | WO 98/44333 | 10/1998 |
| WO | WO 99/044593 | 9/1999 |
| WO | WO 99/44593 | 9/1999 |
| WO | WO 01/022741 | 3/2001 |
| WO | WO 02/12854 | 2/2002 |

OTHER PUBLICATIONS

Bacus, J. et al., "Image Processing for Automated Erythrocyte Classification", *The Journal of Histochemistry and Cytochemistry*, vol. 24:195-201 (1976).

Bacus, J., "Cytometric approaches to red blood cells," *Pure & Appl. Chem.*, vol. 57:593-98 (1985).

Bacus, J., "Digital Image Processing Measurements of Red Blood Cell Size and Hemoglobin Content," *Advances in Hematological Methods: The Blood Count*, Ch. 14, 157-81 (1982).

Bacus, J., "Quantitative Morphological Analysis of Red Blood Cells," *Blood Cells*, vol. 6:295-314 (1980).

Bacus, J., "Quantitative Red Cell Morphology," Monogr. Clin. Cytol., vol. 9:1-27 (1984).

Brochure for BioScan® OPTIMASD™, "Software for image measurement and analysis", *BioScan Incorporated* (1990).

diff3®, "The automation that you need . . . ".

Smeulders, A. et al., "Accuracy of optical density measurement of cells. 1: Low resolution", *Applied Optics*, vol. 26:3249-57 (1987).

Tatsumi, N. et al., "Automated Image Processing: Past, Present, and Future of Blood Cell Morphology Identification", *Clinics in Laboratory Medicine*, vol. 22:299-315 (2002).

Office Action in U.S. Appl. No. 13/446,967, dated Jun. 26, 2012.

International Search Report and Written Opinion issued in application No. PCT/US2012/033636, dated Jun. 29, 2012.

* cited by examiner

MEASURING VOLUME AND CONSTITUENTS OF CELLS

CROSS-REFERENCE TO RELATED APPLICATIONS

This application claims priority under 35 U.S.C. §119(e) to the following U.S. Provisional Patent Applications: 61/476,170, filed on Apr. 15, 2011; 61/476,179, filed on Apr. 15, 2011; 61/510,614, filed on Jul. 22, 2011; 61/510,710, filed on Jul. 22, 2011; and 61/589,672, filed on Jan. 23, 2012. The entire contents of each of the foregoing applications are incorporated by reference herein.

TECHNICAL FIELD

This disclosure relates to measurement of the volume and constituents of blood cells including, but not limited to, red blood cells, platelets, and white blood cells.

BACKGROUND

The volume of blood cells, such as a red blood cells (RBCs) or platelets, is an important metric that can be used to determine other physiologically and therapeutically relevant quantities. For example, the mean cell volume measurement of a patient's red blood cells can be used to assess whether the patient suffers from anemia. Measurement of blood cell constituents is another important metric that can be used for a variety of diagnostic purposes. For example, the mean cell hemoglobin content of a patient's red blood cells also can be used to assess whether a patient suffers from anemia. Such relevant quantities of cell volumes and constituents such as hemoglobin can then be used for a variety of diagnostic purposes, including identifying disease conditions present in a patient, and evaluating possible therapeutic courses of action.

SUMMARY

In general, in a first aspect, the disclosure features methods of determining a hemoglobin content value of a red blood cell, the methods including: (a) illuminating the cell with incident light at a plurality of illumination wavelengths; (b) obtaining at least one two-dimensional image of the cell corresponding to each illumination wavelength; (c) for each illumination wavelength, determining a mean optical density and a maximum optical density for the cell; (d) determining an area of the cell; (e) for each illumination wavelength, determining a volume of the cell based on the area of the cell and the mean optical density and maximum optical density for the cell corresponding to the illumination wavelength; (f) for each illumination wavelength, determining an integrated optical density for the cell based on the area of the cell and the mean optical density for the cell corresponding to the illumination wavelength; and (g) determining the hemoglobin content value of the cell based on a weighted combination of the area of the cell, the volumes of the cell corresponding to each of the illumination wavelengths, and the integrated optical densities for the cell corresponding to each of the illumination wavelengths.

In another aspect, the disclosure features methods of determining a volume of a platelet, the methods including: (a) illuminating the platelet with incident light at a plurality of illumination wavelengths; (b) obtaining at least one two-dimensional image of the platelet corresponding to each illumination wavelength; (c) for each illumination wavelength, determining a mean optical density and a maximum optical density for the platelet; (d) determining an area of the platelet; (e) for each illumination wavelength, determining a volume of the platelet based on the area of the platelet and the mean optical density and maximum optical density for the platelet corresponding to the illumination wavelength; (f) for each illumination wavelength, determining an integrated optical density for the platelet based on the area of the platelet and the mean optical density for the platelet corresponding to the illumination wavelength; and (g) determining the volume of the platelet based on a weighted combination of the area of the platelet, the volumes of the platelet corresponding to each of the illumination wavelengths, and the integrated optical densities for the platelet corresponding to each of the illumination wavelengths.

In a further aspect, the disclosure features methods of determining a volume of a cell, the methods including: (a) illuminating the cell with incident light at a plurality of illumination wavelengths; (b) obtaining at least one two-dimensional image of the cell corresponding to each illumination wavelength; (c) for each illumination wavelength, determining a mean optical density and a maximum optical density for the cell; (d) determining an area of the cell; (e) for each illumination wavelength, determining a volume of the cell based on the area of the cell and the mean optical density and maximum optical density for the cell corresponding to the illumination wavelength; (f) for each illumination wavelength, determining an integrated optical density for the cell based on the area of the cell and the mean optical density for the cell corresponding to the illumination wavelength; and (g) determining the volume of the cell based on a weighted combination of the area of the cell, the volumes of the cell corresponding to each of the illumination wavelengths, and the integrated optical densities for the cell corresponding to each of the illumination wavelengths.

In another aspect, the disclosure features systems for determining a hemoglobin content value of a red blood cell, the systems including an illumination source configured to illuminate the cell with incident light at a plurality of illumination wavelengths, a detector configured to obtain at least one two-dimensional image of the cell corresponding to each illumination wavelength, and an electronic processor configured to: (a) determine a mean optical density and a maximum optical density for the cell at each illumination wavelength; (b) determine an area of the cell; (c) for each illumination wavelength, determine a volume of the cell based on the area of the cell and the mean optical density and maximum optical density for the cell corresponding to the illumination wavelength; (d) for each illumination wavelength, determine an integrated optical density for the cell based on the area of the cell and the mean optical density for the cell corresponding to the illumination wavelength; and (e) determine the hemoglobin content value of the cell based on a weighted combination of the area of the cell, the volumes of the cell corresponding to each of the illumination wavelengths, and the integrated optical densities for the cell corresponding to each of the illumination wavelengths.

In a further aspect, the disclosure features systems for determining a volume of a platelet, the systems including an illumination source configured to illuminate the platelet with incident light at a plurality of illumination wavelengths, a detector configured to obtain at least one two-dimensional image of the platelet corresponding to each illumination wavelength, and an electronic processor configured to: (a) determine a mean optical density and a maximum optical density for the platelet at each illumination wavelength; (b) determine an area of the platelet; (c) for each illumination wavelength, determine a volume of the platelet based on the area of the platelet and the mean optical density and maximum optical density for the platelet corresponding to the illumination wavelength; (d) for each illumination wavelength, determine an integrated optical density for the platelet based on the area of the platelet and the mean optical density for the platelet corresponding to the illumination wavelength; and (e) determine the volume of the platelet based on a weighted combination of the area of the platelet, the volumes of the platelet corresponding to each of the illumination wavelengths, and the integrated optical densities for the platelet corresponding to each of the illumination wavelengths.

In another aspect, the disclosure features systems for determining a volume of a cell, the systems including an illumination source configured to illuminate the cell with incident light at a plurality of illumination wavelengths, a detector configured to obtain at least one two-dimensional image of the cell corresponding to each illumination wavelength, and an electronic processor configured to: (a) determine a mean optical density and a maximum optical density for the cell at each illumination wavelength; (b) determine an area of the cell; (c) for each illumination wavelength, determine a volume of the cell based on the area of the cell and the mean optical density and maximum optical density for the cell corresponding to the illumination wavelength; (d) for each illumination wavelength, determine an integrated optical density for the cell based on the area of the cell and the mean optical density for the cell corresponding to the illumination wavelength; and (e) determine the volume of the cell based on a weighted combination of the area of the cell, the volumes of the cell corresponding to each of the illumination wavelengths, and the integrated optical densities for the cell corresponding to each of the illumination wavelengths.

In a further aspect, the disclosure features methods for determining a mean cell volume for a blood sample, the methods including: illuminating the sample with incident light at a plurality of illumination wavelengths and obtaining a two-dimensional image of the sample at each of the plurality of illumination wavelengths; identifying a plurality of cells that appear in each of the images; for each one of the plurality of cells, determining an integrated optical density corresponding to each of the plurality of illumination wavelengths; for each one of the plurality of cells, determining a cell volume based on the integrated optical densities corresponding to each of the plurality of illumination wavelengths; and determining the mean cell volume for the blood sample from the cell volumes for each one of the plurality of cells.

In another aspect, the disclosure features methods for determining a mean platelet volume for a blood sample, the methods including: illuminating the sample with incident light at a plurality of illumination wavelengths and obtaining a two-dimensional image of the sample at each of the plurality of illumination wavelengths; identifying a plurality of platelets that appear in each of the images; for each one of the plurality of platelets, determining an integrated optical density corresponding to each of the plurality of illumination wavelengths; for each one of the plurality of platelets, determining a platelet volume based on the integrated optical densities corresponding to each of the plurality of illumination wavelengths; and determining the mean platelet volume for the blood sample from the cell volumes for each one of the plurality of cells.

In a further aspect, the disclosure features methods for determining a mean cell hemoglobin value for a blood sample, the methods including: illuminating the sample with incident light at a plurality of illumination wavelengths and obtaining a two-dimensional image of the sample at each of the plurality of illumination wavelengths; identifying a plurality of cells that appear in each of the images; for each one of the plurality of cells, determining an integrated optical density corresponding to each of the plurality of illumination wavelengths; for each one of the plurality of cells, determining a cell hemoglobin value based on the integrated optical densities corresponding to each of the plurality of illumination wavelengths; and determining the mean cell hemoglobin value for the blood sample from the cell hemoglobin values for each one of the plurality of cells.

In another aspect, the disclosure features systems for determining a mean cell volume for a blood sample, the systems including an illumination source configured to direct incident light at a plurality of illumination wavelengths to the sample, a detector configured to obtain two-dimensional images of the sample at each of the plurality of illumination wavelengths, and an electronic processor configured to: identify a plurality of cells that appear in each of the images; for each one of the plurality of cells, determine an integrated optical density corresponding to each of the plurality of illumination wavelengths; for each one of the plurality of cells, determine a cell volume based on the integrated optical densities corresponding to each of the plurality of illumination wavelengths; and determine the mean cell volume for the blood sample from the cell volumes for each one of the plurality of cells.

In a further aspect, the disclosure features systems for determining a mean platelet volume for a blood sample, the systems including an illumination source configured to direct incident light at a plurality of illumination wavelengths to the sample, a detector configured to obtain two-dimensional images of the sample at each of the plurality of illumination wavelengths, and an electronic processor configured to: identify a plurality of platelets that appear in each of the images; for each one of the plurality of platelets, determine an integrated optical density corresponding to each of the plurality of illumination wavelengths; for each one of the plurality of platelets, determine a platelet volume based on the integrated optical densities corresponding to each of the plurality of illumination wavelengths; and determine the mean platelet volume for the blood sample from the platelet volumes for each one of the plurality of cells.

In another aspect, the disclosure features systems for determining a mean cell hemoglobin value for a blood sample, the systems including an illumination source configured to direct incident light at a plurality of illumination wavelengths to the sample, a detector configured to obtain two-dimensional images of the sample at each of the plurality of illumination wavelengths, and an electronic processor configured to: identify a plurality of cells that appear in each of the images; for each one of the plurality of cells, determine an integrated optical density corresponding to each of the plurality of illumination wavelengths; for each one of the plurality of cells, determine a cell hemoglobin value based on the integrated optical densities corresponding to each of the plurality of illumination wavelengths; and determine the mean cell hemoglobin value for the blood sample from the cell volumes for each one of the plurality of cells.

In a further aspect, the disclosure features computer readable storage devices having encoded thereon computer readable instructions that, when executed by a processor, cause the processor to: receive a plurality of images of a blood sample, each of the plurality of images corresponding to a different wavelength of illumination light incident on the sample; identify a plurality of cells that appear in each of the images; for each one of the plurality of cells, determine an integrated optical density corresponding to each of the plurality of illumination wavelengths; for each one of the plurality of cells, determine a cell volume based on the integrated optical densities corresponding to each of the plurality of illumination wavelengths; and determine a mean cell volume for the blood sample from the cell volumes for each one of the plurality of cells.

In another aspect, the disclosure features computer readable storage devices having encoded thereon computer readable instructions that, when executed by a processor, cause the processor to: receive a plurality of images of a blood sample, each of the plurality of images corresponding to a different wavelength of illumination light incident on the sample; identify a plurality of platelets that appear in each of the images; for each one of the plurality of platelets, determine an integrated optical density corresponding to each of the plurality of illumination wavelengths; for each one of the plurality of platelets, determine a platelet volume based on the integrated optical densities corresponding to each of the plurality of illumination wavelengths; and determine a mean platelet volume for the blood sample from the cell volumes for each one of the plurality of cells.

In a further aspect, the disclosure features computer readable storage devices having encoded thereon computer readable instructions that, when executed by a processor, cause the processor to: receive a plurality of images of a blood sample, each of the plurality of images corresponding to a different wavelength of illumination light incident on the sample; identify a plurality of cells that appear in each of the images; for each one of the plurality of cells, determine an integrated optical density corresponding to each of the plurality of illumination wavelengths; for each one of the plurality of cells, determine a cell hemoglobin value based on the integrated optical densities corresponding to each of the plurality of illumination wavelengths; and determine a mean cell hemoglobin value for the blood sample from the cell volumes for each one of the plurality of cells.

Embodiments of the methods, systems, and devices can include any one or more of the following features.

The methods can include repeating steps (a) through (g) for a plurality of red blood cells from a sample of blood to determine hemoglobin content values for each one of the plurality of red blood cells, and determining a mean cell hemoglobin value for the sample from the hemoglobin content values for each one of the plurality of red blood cells.

The methods can include identifying a first set of pixels in each image of the cell that corresponds to the cell. The methods can include identifying a second set of pixels in each image that corresponds to the cell by removing pixels from the first set of pixels that correspond to a perimeter region of the cell. The methods can include determining the area of the cell based on the first set of pixels.

The methods can include determining a perimeter of the cell based on the first set of pixels, and excluding the cell from the determination of the mean cell hemoglobin value if a ratio of the perimeter squared to the area exceeds a threshold value. The methods can include determining a convex hull of the cell, determining an area enclosed by the convex hull, and excluding the cell from the determination of the mean cell hemoglobin value if a ratio of the area enclosed by the convex hull to the area of the cell exceeds a threshold value. The methods can include excluding the cell from the determination of the mean cell hemoglobin value if the area of the cell is outside a selected area range.

The methods can include determining the volume of the cell at each illumination wavelength based on a ratio of the mean optical density to the maximum optical density corresponding to the illumination wavelength. The methods can include determining the volume of the cell at each illumination wavelength based on a ratio of the mean optical density to the sum of the maximum optical density and a correction factor at the illumination wavelength. The methods can include adding an offset value to the ratio of the mean optical density to the sum of the maximum optical density and the correction factor to determine the volume of the cell at each illumination wavelength. The methods can include determining values of the correction factor and the offset value from a reference set of blood samples.

The plurality of illumination wavelengths can include at least three illumination wavelengths. The plurality of illumination wavelengths can include at least one wavelength between 575 nm and 600 nm, at least one wavelength between 525 nm and 570 nm, and at least one wavelength between 400 nm and 475 nm. The plurality of illumination wavelengths can include at least four illumination wavelengths. The plurality of illumination wavelengths can include at least one wavelength between 620 nm and 750 nm, at least one wavelength between 575 nm and 600 nm, at least one wavelength between 525 nm and 570 nm, and at least one wavelength between 400 nm and 475 nm.

Assessing an operating condition of an automated blood analysis device can include operating the device so that the device uses the methods disclosed herein to determine a mean cell hemoglobin value for a control composition, and comparing a reference value of the mean cell hemoglobin for the control composition to the determined value of the mean cell hemoglobin to assess the operating condition of the device. Assessing the operating condition of the device can include determining a difference between the determined and reference values of the mean cell hemoglobin for the control composition, re-calibrating the device if the difference exceeds a threshold value. Re-calibrating the device can include determining, from a reference set of blood samples, a plurality of weight coefficients that are used to determine the hemoglobin content value of the cell based on the area of the cell, the volumes of the cell corresponding to each of the illumination wavelengths, and the integrated optical densities for the cell corresponding to each of the illumination wavelengths.

The electronic processor can be configured to repeat steps (a) through (e) for a plurality of red blood cells from a sample of blood to determine hemoglobin content values for each of the plurality of red blood cells, and determine a mean cell hemoglobin value for the sample from the hemoglobin content values for each of the plurality of red blood cells.

The systems can include an automated blood sample preparation system.

The methods can include repeating steps (a) through (g) for a plurality of platelets or cells from a sample of blood to determine volumes for each of the plurality of platelets or cells, and determining a mean platelet volume or a mean cell volume for the sample from the volumes for each of the plurality of platelets. The methods can include identifying a set of pixels in each image of the platelet or cell that corresponds to the platelet or cell. Identifying the set of pixels can include identifying a first set of pixels that corresponds to a central region of the platelet, identifying a second set of pixels that corresponds to a non-central region of the platelet, and merging the first and second sets of pixels to form the set of pixels that corresponds to the platelet. The methods can include identifying the second set of pixels based on intensity values for each member of the set of pixels in at least two images corresponding to different illumination wavelengths.

The plurality of illumination wavelengths can include an illumination wavelength in a blue region of the electromagnetic spectrum and an illumination wavelength in a yellow region of the electromagnetic spectrum, and the methods can include obtaining an image of the platelet corresponding to the illumination wavelength in the blue region and an image of the platelet corresponding to the illumination wavelength in the yellow region. The methods can include excluding the platelet from the determination of the mean platelet volume if an integrated optical density for the platelet in the image corresponding to the illumination wavelength in the yellow region is larger than 600. The methods can include excluding the platelet from the determination of the mean platelet volume if an integrated optical density for the platelet in the image corresponding to the illumination wavelength in the blue region is larger than 200. The methods can include determining the area of the platelet or cell based on the set of pixels.

The methods can include determining the volume of the platelet or cell at each illumination wavelength based on a ratio of the mean optical density to the maximum optical density corresponding to the illumination wavelength. The methods can include determining the volume of the platelet or cell at each illumination wavelength based on a ratio of the mean optical density to the sum of the maximum optical density and a correction factor at the illumination wavelength. The methods can include adding an offset value to the ratio of the mean optical density to the sum of the maximum optical density and the correction factor to determine the volume of the platelet or cell at each illumination wavelength.

Assessing an operating condition of an automated blood analysis device can include operating the device so that the device uses the methods disclosed herein to determine a mean platelet volume or mean cell volume for a control composition, and comparing a reference value of the mean platelet volume or the mean cell volume for the control composition to the determined value of the mean platelet volume or the mean cell volume to assess the operating condition of the device. Assessing the operating condition of the device can include determining a difference between the determined and reference values of the mean platelet volume or mean cell volume for the control composition, and re-calibrating the device if the difference exceeds a threshold value. Re-calibrating the device can include determining, from a reference set of blood samples, a plurality of weight coefficients that are used to determine the volume of the platelet or the volume of the cell based on the area of the platelet or cell, the volumes of the platelet or cell corresponding to each of the illumination wavelengths, and the integrated optical densities for the platelet or cell corresponding to each of the illumination wavelengths.

The electronic processor can be configured to repeat steps (a) through (e) for a plurality of platelets or cells from a sample of blood to determine volumes for each of the plurality of platelets or cells, and determine a mean platelet volume or a mean cell volume for the sample from the volumes for each of the plurality of platelets or cells.

The methods can include: for each one of the plurality of cells or platelets, determining a volume corresponding to each of the plurality of illumination wavelengths; and for each one of the plurality of cells or platelets, determining the cell or platelet volume based on the integrated optical densities and the volumes corresponding to each of the plurality of illumination wavelengths. The methods can include: for each one of the plurality of cells or platelets, determining an area of the cell or platelet; and for each one of the plurality of cells or platelets, determining the cell or platelet volume based on the area of the cell or platelet and the integrated optical densities corresponding to each of the plurality of illumination wavelengths. The methods can include: for each one of the plurality of cells or platelets, determining an area of the cell or platelet; and for each one of the plurality of cells or platelets, determining the cell or platelet volume based on the area of the cell or platelet and the integrated optical densities and volumes corresponding to each of the plurality of illumination wavelengths.

Each two-dimensional image can correspond to incident light that is reflected from, or transmitted by, the sample.

The perimeter region of the cell can have a thickness of 0.5 microns or more.

The methods can include, for each one of the plurality of cells or platelets, determining a convex hull of the cell or platelet, determining an area enclosed by the convex hull, and excluding the cell or platelet from the determination of the mean cell volume or mean platelet volume if a ratio of the area enclosed by the convex hull to an area of the cell or platelet exceeds a threshold value.

The methods can include, for each one of the plurality of cells or platelets, excluding the cell or platelet from the determination of the mean cell or platelet volume if the area of the cell or platelet is outside a selected area range.

For each one of the plurality of cells or platelets, determining the integrated optical density corresponding to each of the plurality of illumination wavelengths can include determining an area of the cell or platelet, determining for each of the plurality of illumination wavelengths a mean optical density for the cell or platelet based a corresponding one of the images, and determining the integrated optical density corresponding to each wavelength based on the area of the cell or platelet and the mean optical density for the cell or platelet corresponding to the wavelength.

For each one of the plurality of cells or platelets, determining the volume corresponding to each of the plurality of illumination wavelengths can include: for each of the plurality of illumination wavelengths, determining a mean optical density and a maximum optical density for the cell or platelet; and for each of the plurality of illumination wavelengths, determining the volume of the cell or platelet based on a ratio of the mean optical density to the maximum optical density corresponding to the wavelength.

For each one of the plurality of cells or platelets, determining the volume corresponding to each of the plurality of illumination wavelengths can include: for each of the plurality of illumination wavelengths, determining a mean optical density and a maximum optical density for the cell or platelet; and for each of the plurality of illumination wavelengths, determining the volume of the cell or platelet based on a ratio of the mean optical density to the sum of the maximum optical density corresponding to the wavelength and a correction factor at the wavelength. The methods can include adding an offset value to the ratio of the mean optical density to the sum of the maximum optical density and the correction factor to determine the volume of the cell or platelet at each illumination wavelength.

For each one of the plurality of cells or platelets, the cell or platelet volume can be determined based on a weighted linear combination of the integrated optical densities corresponding to each of the plurality of illumination wavelengths. For each one of the plurality of cells or platelets, the cell or platelet volume can be determined based on a weighted linear combination of the integrated optical densities and the volumes corresponding to each of the plurality of illumination wavelengths. For each one of the plurality of cells or platelets, the cell or platelet volume can be determined based on a weighted linear combination of the area and the integrated optical densities and volumes corresponding to each of the plurality of illumination wavelengths. The methods can include determining weight coefficients for the weighted linear combination from a reference set of blood samples.

Re-calibrating the device can include determining, from a reference set of blood samples, a plurality of weight coefficients that are used to determine the cell or platelet volume based on the integrated optical densities corresponding to each of the plurality of illumination wavelengths.

The electronic processor can be configured to: for each one of the plurality of cells or platelets, determine a volume corresponding to each of the plurality of illumination wavelengths; and for each one of the plurality of cells or platelets, determine the cell or platelet volume based on the integrated optical densities and the volumes corresponding to each of the plurality of illumination wavelengths. The electronic processor can be configured to: for each one of the plurality of cells or platelets, determine an area of the cell or platelet; and for each one of the plurality of cells or platelets, determine the cell or platelet volume based on the area and the integrated optical densities corresponding to each of the plurality of illumination wavelengths. The electronic processor can be configured to: for each one of the plurality of cells or platelets, determine an area of the cell; and for each one of the plurality of cells or platelets, determine the cell or platelet volume based on the area and the integrated optical densities and volumes corresponding to each of the plurality of illumination wavelengths.

Embodiments of the methods, systems, and devices can also include any of the other features and steps disclosed herein, as appropriate.

Although specific combinations of features and embodiments are described, any of the features disclosed herein can be combined and sub-combined with any of the other features disclosed herein in the methods, systems, and devices, except where expressly precluded. Accordingly, it is to be understood that embodiments of the methods, systems, and devices disclosed herein can include any combination of the features described in connection with any of the embodiments disclosed herein. Moreover, the embodiments of the methods, systems, and devices disclosed herein can include any combination of the features disclosed herein and any of the features disclosed in connection with any of the embodiments in U.S. Provisional Patent Applications: 61/476,170; 61/476,179; 61/510,614; 61/510,710; and 61/589,672.

Unless otherwise defined, all technical and scientific terms used herein have the same meaning as commonly understood by one of ordinary skill in the art to which this disclosure belongs. Although methods and materials similar or equivalent to those described herein can be used in practice or testing, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments are set forth in the accompanying drawings and the description below. Other features and advantages will be apparent from the description, drawings, and claims.

DESCRIPTION OF DRAWINGS

Like reference symbols in the various drawings indicate like elements.

DETAILED DESCRIPTION

Figure 1A:
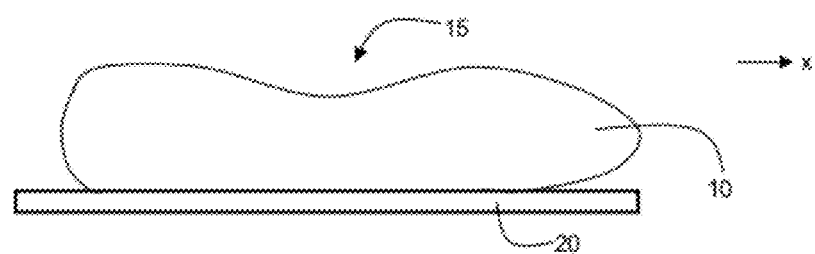
FIG. 1A is a schematic diagram of a red blood cell positioned on a substrate.

Manual analysis of blood samples—which typically involves preparing a blood smear on a glass slide and then evaluating the smear under a microscope—suffers from a number of disadvantages that make such methods unsuitable for use in high-throughput environments. Human technician preparation of blood smears is prone to non-systematic errors, particularly the non-uniform distribution of blood throughout the smear. Frequently, certain regions of such smears are thicker than other regions, making accurate quantitative analysis by a user difficult unless significant compromises are accepted (e.g., examining only a small region of the overall smear, which region typically differs in size and location from smear to smear). Further, when stains are applied to blood samples, variations in the staining protocol from one sample to another can occur as a result of human error. These variations can, in turn, cause variations in quantitative measurements taken from the samples that do not necessarily correspond to underlying variations in quantities of cellular constituents in the sample. Moreover, human technician preparation of individual blood smears is a time-consuming process, and can result in the use of large quantities of preparative solutions (e.g., stains, rinsing solutions, buffer solutions, fixatives). Consumption of such solutions can be costly. Further, the generation of large volumes of these solutions also introduces difficulties and costs related to the disposal of waste volumes of the solutions.

Current automated sample preparation systems can significantly reduce non-systematic errors associated with manual preparation processes. Variations still exist, however, in prepared samples using such systems. For example, with a sample of blood prepared on a microscope slide, automated stainers may not uniformly stain the entire sample; depending on sample thickness, sample drying time, and other variables associated with the sample preparation and staining process, the sample may exhibit portions with varying levels of stain concentrations in the cells.

Disclosed herein are methods and systems for automated measurement of the volumes of individual cells and the concentrations of cellular constituents in cells of prepared biological samples. The methods and systems can be used on samples that are manually prepared by a trained human operator. In addition, the methods and systems can be used to analyze samples prepared in an automated system. In this way, the methods and systems disclosed herein permit high-throughput, fully-automated analysis of a variety of biological samples extracted from patients.

By way of example, the present disclosure describes measuring the volumes and determining the hemoglobin content of individual red blood cells in a blood sample taken from a human patient. However, the disclosure is not limited to such applications. In particular, the methods and systems disclosed herein can be used to measure, in an automated fashion, volumes of a variety of different types of cells including platelets. In addition, other cellular constituents such as proteins other than hemoglobin can be measured using the methods and systems disclosed herein. Moreover, the samples to be analyzed need not be from human patients; the methods and systems disclosed herein can also be used on samples from animals, or on compositions designed to mimic whole blood to control, calibrate, and verify the linearity of results obtained from an automated hematology system.

Automated systems for measuring cell volumes and cell constituents from prepared biological samples will be described in greater detail below. Once a sample is prepared, it is transported to the automated measurement system. The measurement system acquires one or more two-dimensional images of the cells in the sample, and uses the images to determine, among other quantities, the volumes and hemoglobin content of cells within the sample. The volumes and hemoglobin content of cells are determined from information derived from images of the cells obtained by directing incident light on the cells, and then detecting the portion of the incident light that is either transmitted through, or reflected from, the cells. Each image is a two-dimensional image, where an individual pixel intensity value within the image corresponds to the amount of transmitted or reflected light emerging from a spatial location on the cell that corresponds to the pixel.

General Considerations

The volume of any cell, such as a red blood cell or platelet, is a three-dimensional quantity. Determining the cell volume based on information derived from a two-dimensional image of the cell is one of the challenges that is addressed herein. Obtaining a measurement of the cell volume from a two-dimensional image involves estimating the shape of the cell in the direction transverse to the two-dimensional plane of the image from information derived from the image. If all cells were the same shape, determining the volume would be relatively straightforward: the volume of any such cell would be proportional to the cross-sectional area of the cell (which can be obtained from a two-dimensional image) raised to the 3/2 power. Cells are not uniformly shaped, however, so the above assumption is not reliable in all instances or sufficiently accurate for diagnostic purposes.

Figure 1B:
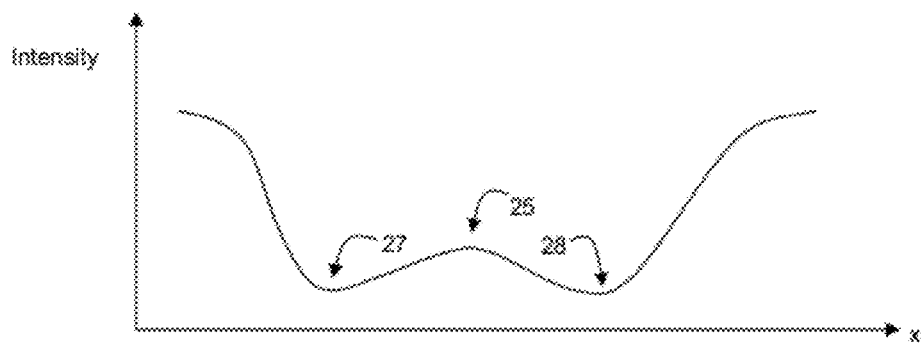
FIG. 1B is a schematic plot showing transmitted light intensity as a function of position for the cell of FIG. 1A.

As an example, red blood cells typically exhibit a variety of shapes: some are approximately spherical, while others have a shape that is closer to toroidal. In addition, red blood cells have a central indentation of variable depth. Images of such cells depict edge regions where the intensity of transmitted light is relatively smaller, and a central region of increased light transmission referred to as the "central pallor." FIG. 1A is a schematic diagram showing a red blood cell 10 positioned on a substrate 20. The thickness of cell 10 along the x-direction varies; the thickness is largest near the edges of the cell and reduced in the center region 15 of the cell. FIG. 1B is a schematic plot of transmitted light intensity as a function of position along the x-direction for a particular cross-sectional position through the transmitted light distribution from cell 10. The intensity distribution shown in FIG. 1B includes a local intensity maximum 25 within the central pallor of the cell, and local intensity minima 27 and 28 of lower light transmission that corresponds to the edges of the cell. Even unstained red blood cells will exhibit the phenomenon shown in FIG. 1B because these cells contain hemoglobin, which absorbs blue light.

Cell 10 is typically prepared (as part of a sample) by applying one or more stains to the cell to obtain the intensity distribution shown in FIG. 1B. The stain binds to the cell's cytoplasm, and serves as a marker for the cytoplasm in cell images. When the cell is illuminated with incident light, the stain absorbs a portion of the incident light; the amount of absorption at a particular location in the sample depends on the amount of stain present at that location. If it is assumed that the applied stain binds in a uniform manner to all cytoplasm, then the transmitted light intensity at a given image pixel should be proportional to the thickness of the cytoplasm at a corresponding location within the cell. As such, a quantity proportional to a cell volume could be obtained by summing contributions to the transmitted light intensity from all pixels within an image that correspond to the particular cell. In practice, however, prepared samples of blood cells exhibit some variability in the extent that applied stains uniformly bind to all cytoplasm.

The amount of transmitted light at each pixel location, however, also depends on amounts of various sample constituents—such as hemoglobin in red blood cells—present at each location in a cell. Further, the distribution of stain from one spatial location to the next also affects the amount of measured transmitted light at each pixel location for a given cell or blood constituent.

In view of these considerations, the methods and systems disclosed herein are adapted to determine cell volume based on information derived from two-dimensional cell images by decoupling the estimate of cell thickness from the absorptive effects of locally-varying concentrations of cellular constituents (e.g., hemoglobin) and various applied stains. To implement such decoupling, pixel intensities are scaled according to the maximum pixel intensity for each cell. As further described below, cell volume calculations are based on a weighted combination of optical density values for each color of illumination used to acquire cell images, and cell area. The processes described herein can be repeated for each member of a set of cells selected for volume measurement, and the results for each cell can be used to calculate a mean cell volume for the sample.

Concentrations of cellular constituents, such as hemoglobin content of red blood cells, also can be determined from calculations based on optical density values for each color of illumination used to acquire cell images, as will be described further below, and the following disclosure also encompasses methods and systems for automated measurement of one or more constituents of cells from prepared biological samples. By way of example, the present disclosure focuses on the measurement of hemoglobin in red blood cells in a blood sample taken from a human patient. However, it is to be understood that the disclosure is not limited to such applications. In particular, the methods and systems disclosed herein can be used to measure, in automated fashion, a variety of different constituents in a variety of different types of cells. Moreover, cell samples need not be taken from human patients; the methods and systems disclosed herein can also be used on samples taken from animals, or on compositions manufactured to mimic whole blood, which are typically used to verify the performance of an automated measurement system.

Conventional automated measurement systems, such as flow cytometers, typically determine cellular hemoglobin content by lysing red blood cells and measuring the absorbance of the lysed sample in solution, or by measuring light scattered from individual red blood cells in a flow stream. The methods and systems disclosed herein can be implemented without lysing of any component of the blood sample or a flow cell. Rather, cellular constituents such as hemoglobin can be measured from two-dimensional images of a sample deposited on a microscope slide, which preserves the natural morphology of the cells for other measurements and classification.

The sample preparation process for utilizing the automated methods and systems described herein typically involves applying multiple stains to the sample. The applied stains bind differently to different chemical and/or structural entities within the sample, permitting selective analysis of different sample features (e.g., certain stains bind preferentially to blood cell nuclei, while others bind to cell membranes, and still others may bind preferentially to certain constituents within the cytoplasm). In turn, the applied stains enable automated systems to perform several measurements on the sample such as identifying and counting red blood cells, white blood cells, and platelets, and performing a five-part white blood cell differential. With multiple stains present in the samples, however, spectroscopic measurements performed on the samples can conceivably suffer from interfering effects produced by the various stains. For example, at a given measurement wavelength, multiple stains may be significant absorbers of incident light. The methods and systems disclosed herein account for the presence of multiple spectral contributors (e.g., absorbing stains and/or cellular constituents) within a sample, and determine amounts of one or more contributors present in the cells based on information measured at multiple wavelengths.

The amount of hemoglobin in red blood cells is a quantity of interest, as the cellular hemoglobin content can be used to calculate a variety of blood-related quantities for a sample (e.g., mean cell hemoglobin concentration, hematocrit) that are used by physicians for diagnostic purposes. Hemoglobin absorbs incident light more strongly within certain regions of the electromagnetic spectrum than in others, and therefore has a characteristic spectral signature. When one or more stains are applied to a sample, the stain(s) also have characteristic spectral signatures and absorb incident light more strongly at certain wavelengths than others. In many applications, both an analyte of interest such as hemoglobin and one or more applied stains may have non-negligible absorption at particular wavelengths. In such applications, the amount of incident light transmitted through the sample at a particular wavelength is related to the amount of absorption by hemoglobin, by the other stains applied to the sample, and by the other sample constituents.

For purposes of the following disclosure and certain examples, at least two stains are assumed to be applied to the samples: eosin and azure. However, the methods and systems disclosed herein are not limited to application of only two stains or solely to eosin and azure. To the contrary, the methods and systems are capable of performing measurements on samples to which fewer stains (e.g., one stain, or no stains) or more stains (e.g., a red stain comprising eosin and a blue stain comprising azure and methylene blue, three or more stains, four or more stains, five or more stains) have been applied.

Automated Measurement Systems

Figure 2:
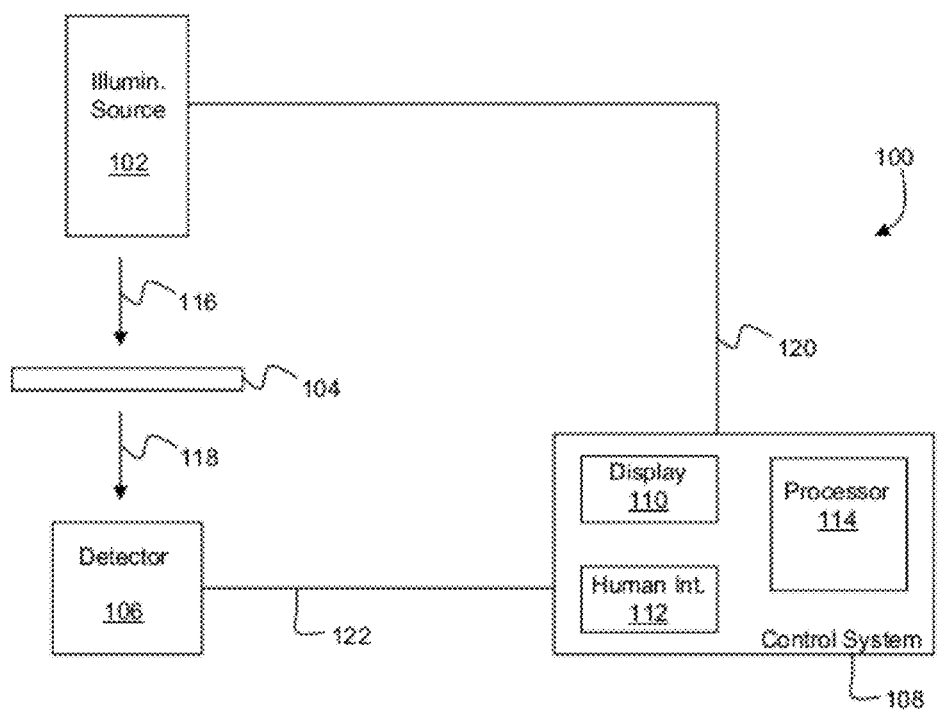
FIG. 2 is a schematic diagram of a system for measuring volumes and constituents of cells in a biological sample.

FIG. 2 shows a schematic diagram of a system 100 (which can be part of a larger sample processing and analysis system) for performing automated measurements of cell volumes and constituents of cells from a biological sample. System 100 includes an illumination source 102, a detector 106, and an electronic control system 108. Electronic control system 108 can include a display 110, a human interface unit 112, and an electronic processor 114. Electronic control system 108 is connected to illumination source 102 and to detector 106 via control lines 120 and 122, respectively.

Assuming that a sample has been prepared (as will be discussed further below) for analysis, the prepared sample 104 (e.g., a blood sample deposited on a microscope slide and subsequently fixed, stained, and rinsed) is positioned automatically in proximity to source 102. Source 102 directs incident light 116 toward sample 104. A portion of the incident light passes through sample 104 as transmitted light 118 and is detected by detector 106. Transmitted light 118 forms an image of sample 104 on the active surface of detector 106; the detector captures the image, and then transmits the image information to electronic control system 108. In general, electronic control system 108 directs source 102 to produce incident light 116, and also directs detector 106 to detect the image of sample 104. Control system 108 can instruct source 102 to use different illumination wavelengths when detector 106 acquires images of sample 104 from transmitted light 118.

The process discussed above can be repeated on multiple images of sample 104 if desired. Prior to acquiring a new image, electronic control system 108 can change the wavelength of incident light 116 produced by source 102. As such, the images of sample 104 each correspond to different wavelengths of incident light 116 and therefore, different wavelengths of transmitted light 118. The process repeats until at least enough information has been acquired to perform an accurate determination of the volume of cells in the sample or the amount of one or more constituents in the sample. Typically, the amount of information that yields an accurate determination of the volume of cells in the sample or the amount of one or more constituents in the sample is determined during a calibration process. For example, the calibration process can be used to determine (as further described below) that accurate determination of the volume of cells in the sample and/or the amount of one or more constituents in the sample can be achieved when the number of sample images obtained is equal to or greater than the number of spectral contributors (e.g., absorbers) factored into the analysis of the sample.

As an example, for a prepared sample comprising red blood cells that include hemoglobin as a naturally-present absorber, and eosin and azure as applied stains (for a total of three spectral contributors), system 100 can continue to acquire sample images until it has obtained images at a minimum of three different wavelengths. Additional images—corresponding to further different wavelengths—can also be obtained and used in the determination of cellular constituents and cell volumes for the sample.

Illumination source 102 can include one source or a plurality of the same or different sources for directing incident light to a sample. In some embodiments, source 102 can include multiple light emitting elements such as diodes (LEDs), laser diodes, fluorescent lamps, incandescent lamps, and/or flashlamps. For example, source 102 can include four LEDs having output wavelengths in the red, yellow, green, and blue regions of the electromagnetic spectrum, respectively (e.g., 635, 598, 525, and 415 nm), or more generally, about 620 to 750 nm (red), about 575 to 600 nm (yellow), about 525 to 570 nm (green), and about 400 to 475 nm (blue).

In certain embodiments, source 102 can include one or more laser sources. Instead of having multiple light emitters, in other embodiments, source 102 can include a single broadband emitter than can be configured to alter its output wavelength (e.g., under the control of electronic control system 108). For example, source 102 can include a broadband source (e.g., an incandescent lamp) coupled to a configurable filter system (e.g., a plurality of mechanically adjustable filters, and/or a liquid-crystal-based electronically-adjustable filter) that produces a variable output spectrum under the control of system 108. In general, source 102 does not output illumination light 116 at a single wavelength, but in a band of wavelengths centered around a central wavelength (e.g., the wavelength of maximum intensity in the band). When the discussion herein refers to the wavelength of illumination light 116, this reference is to the central wavelength of the illumination band.

Detector 106 can include a variety of different types of detectors. In some embodiments, detector 106 includes a charge-coupled device (CCD). In certain embodiments, detector 106 can include photodiodes (e.g., a two-dimensional photodiode array). In some embodiments, detector 106 can include other light-sensitive elements such as CMOS-based sensors and/or photomultipliers. Detector 106 can also include one or more filtering elements, as described above in connection with source 102. In some embodiments, sample images corresponding to different wavelengths are obtained by illuminating sample 104 with illumination light 116 having a relatively broad distribution of wavelengths, and then filtering transmitted light 118 to select only a portion of the transmitted light corresponding to a small band of the wavelengths. Filtering can be performed on either or both the excitation side (e.g., in source 102) and the detection side (e.g., in detector 106) to ensure that images obtained using detector 106 each correspond to a specific distribution of light wavelengths with a particular central wavelength.

General Methodology

Figure 3A:
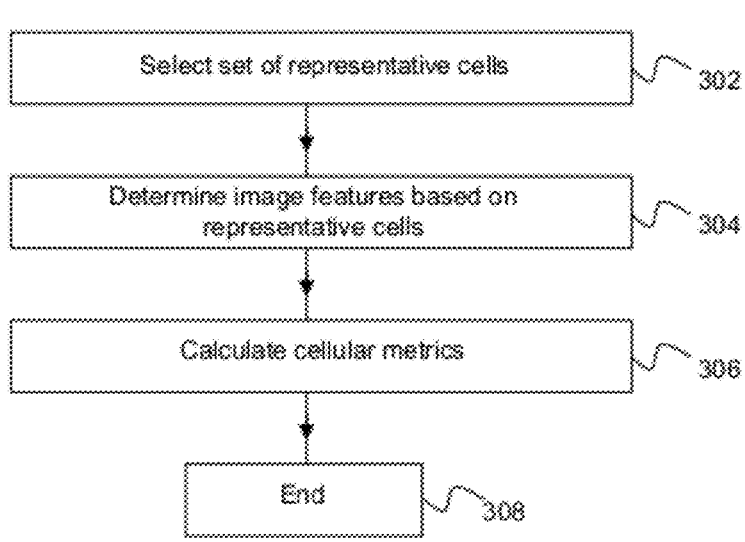
FIG. 3A is a schematic diagram showing a series of steps for determining cellular metrics for cells in a biological sample.

The systems and methods disclosed herein acquire images of cells in a sample (e.g., a blood sample) and determine quantities such as cell volume and the amounts of cellular constituents based on the images. FIG. 3A shows a flowchart 300 that includes various steps for determining these quantities. In a first step 302, a set of representative cells are selected. The images of the cells in the representative set are the ones that are used for subsequent determination of cellular quantities for the sample. In the next step 304, various image features are determined based on the images of the cells in the representative set. As will be discussed below, image features can include intensity values that are measured directly by a detector, and other values that are calculated from image data. In step 306, cellular metrics such as cell volume and the amount of cellular constituents (e.g., hemoglobin) are calculated based on the image features determined in step 304. The process terminates at step 308. Each of the steps in flow chart 300 is described greater detail below.

(i) Selecting a Set of Representative Cells

Before calculating cellular metrics, the systems and methods disclosed herein identify a set of representative cells for further analysis from a plurality of cells in a prepared biological sample. For example and as further described below for blood samples, such systems and methods use optical density measurements obtained from sample images to identify a representative set of red blood cells suitable for volume and constituent analysis. This process typically involves differentiating and excluding other cells types such as white blood cells and platelets, overlapped or misshapen red blood cells, and non-cellular artifacts and debris from further analysis.

Utilizing images acquired via detector 106, intensity values for each pixel in a sample image can be correlated to an optical density value used in the selection of a representative set of cells and subsequent cell volume and constituent analysis. The transmitted light intensity T(x,y) at a given image pixel (x,y) is related to the absorption coefficient α and the path length ϵ(x,y) of the incident light through the portion of the sample corresponding to that pixel:

$$T(x,y)=10^{-\alpha \cdot \epsilon(x,y)} \quad (1)$$

For each pixel in an image, the ratio of the pixel intensity to the maximum possible pixel intensity (e.g., pixel intensity/255 at 8-bit resolution) represents the fraction of light transmitted at the spatial location of the pixel. The fraction of transmitted light can be expressed in optical density (OD) units by taking the logarithm of Equation (1):

$$OD(x,y)=-\log(T)=\alpha \cdot \epsilon(x,y) \quad (2)$$

This process can be repeated for each pixel in the sample image. In this way, the optical density at each pixel in each image corresponds to the total amount (e.g., the product of the absorption coefficient and the thickness) of absorbing material in the sample at the location corresponding to the pixel.

Figure 3B:
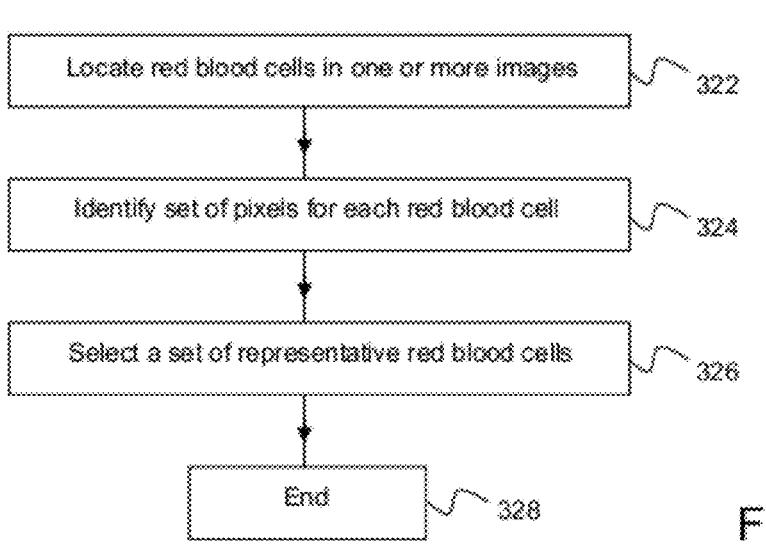
FIG. 3B is a schematic diagram showing a series of steps for selecting a representative set of cells from one or more images of a biological sample.

FIG. 3B shows a flowchart 320 that includes a series of steps for selecting a set of representative red blood cells in a prepared sample of blood. After acquiring images of the sample, electronic control system 108 and, in particular electronic processor 114, processes the image information to differentiate cells for inclusion in the set of representative red blood cells from the other cell types, cell clusters, and artifacts present in the sample.

First, in step 322 of FIG. 3B, system 100 locates red blood cells in one or more sample images for further processing. Red blood cells typically absorb blue light (e.g., 415 nm) due to the presence of hemoglobin in the cells. White blood cells, however, do not contain hemoglobin and therefore do not absorb blue light in the same manner as red blood cells. An image of the sample acquired under blue light can be used to identify red blood cells; white blood cells in such images appear faintly and distorted because these cells minimally absorb blue light, thereby reducing contributions to the image and typically making them unidentifiable.

In some embodiments, a thresholding step can be used to ensure that system 100 identifies only red blood cells for further analysis. For example, system 100 can utilize only image pixels below an intensity (or gray) value of 160 (for images captured at 8-bit resolution). Other intensity value thresholds ranging from 100 to 180 can be used to identify red blood cells from the image, while excluding white blood cells from further analysis.

Next, in step 324, system 100 identifies a set of pixels for each red blood cell in the sample image. A variety of different methods can be used to identify sets of pixels associated with the cells. For example, in some embodiments, system 100 performs the identification step using a connected components labeling process. This process correlates individual pixels from the sample image to an object in the image. For example, any two pixels in the image not separated by a pixel assigned to the background are assigned to the same cell.

In addition, system 100 can exclude pixels positioned within a border region of a cell from certain measurements relating to the cell volume and constituent analysis. In particular, red blood cells often have thick, dark borders due to the manner in which these cells refract illumination light, for example, as shown in FIG. 9. Optical densities for these pixels are typically unreliable due to this refraction. After completing the connected components labeling process, system 100 can apply a pixel erosion mask to the identified cells to remove the outermost n layers of pixels (e.g., the pixel(s) that correspond to the boundary region where refraction is greatest). In general, the pixel erosion mask can be selected to remove any number n of pixel layers (e.g., one pixel layer or more, two pixel layers or more, three pixel layers or more, four pixel layers or more, five pixel layers or more, six pixel layers or more, eight pixel layers or more, ten pixel layers or more) depending on the magnification of the image. It has been determined experimentally that a pixel erosion mask comprising the outermost 0.5 µm for the red cell perimeter is generally suitable for significantly reducing erroneous contributions to the measurement of cell volume and hemoglobin content for red blood cells where each pixel corresponds to a portion of the cell that is 0.148 µm×0.148 µm. Utilizing the sets of pixels corrected by erosion masks, various cell features can be measured, such as a mean and maximum optical density for each cell, which contribute to the cell volume and constituent analysis.

In step 326, system 100 continues the process of identifying a set of representative red blood cells from the sample image(s) by confirming that the set contains only complete and normally shaped and sized red blood cells. In general, step 326 functions to discard partial cells, overlapping cells, cell clusters, platelets, and non-cellular artifacts from inclusion in the set of representative red blood cells. For example, cells that are either cut off by, or touching, the edge of the image frame can be excluded from further analysis, thereby preventing inaccurate measurements. In addition, misshapen cells—which can exhibit variations in the determined cell volume that are related to their non-standard shapes—can be excluded from the analysis. Further, measurement results obtained from overlapping cells, which can be unreliable when used for calculating cell volumes or constituent content, can be precluded from the set of representative cells. For these reasons, the shapes of each of the identified cells are checked in step 326, and misshapen and/or overlapping cells are excluded from further analysis.

Figure 4:
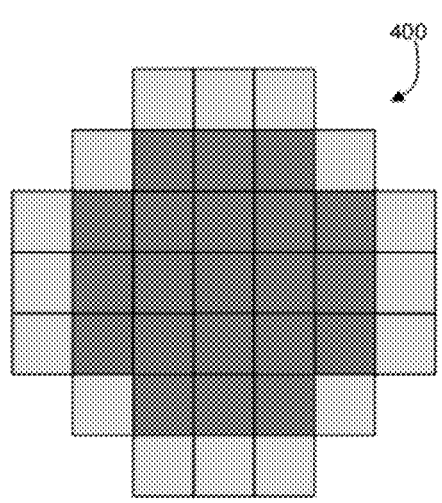
FIG. 4 is a schematic image of a cell showing the cell boundary.

A variety of different methods can be used to check the shape of the identified cells. For example, in some embodiments, the shape of each cell can be checked by comparing the perimeter and the area of the cell. FIG. 4 shows a schematic diagram of such a comparison. In FIG. 4, a cell 400 has been identified as a set of pixels in a sample image. The pixels corresponding to the boundary of cell 400 are shaded lighter in FIG. 4 than the interior pixels for purposes of demonstration—they do not necessarily appear this way in the actual image. The area of cell 400 can be determined by counting the number of pixels in the set.

The cell perimeter is determined from the boundary pixels using the set of pixels corresponding to cell 400. This can be accomplished by connecting a line through the center of each perimeter pixel to create a polygon in the image and measuring the perimeter of the polygon. The ratio of this cell perimeter value squared to the cell area value (i.e., the area of the polygon) is determined to check the shape of the cell. The value of this ratio is $4\pi$ for an ideal, perfectly circular cell. The value of the ratio increases as the cell shape departs from a circular outline. Using this criterion, cells with a ratio of the perimeter squared to the area, which exceeds the minimum value of $4\pi$ by a threshold amount or more, are excluded from further analysis. Typically, the threshold amount is a percentage of the minimum value of $4\pi$ (e.g., 5% or more, 10% or more, 15% or more, 20% or more, 25% or more).

In addition to excluding misshapen individual cells from further analysis, the procedure discussed above can also exclude overlapping cells. In sample images, overlapping cells typically appear as large, misshapen individual cells (with variations in transmitted light intensity due to the increased thickness of material through which the incident light propagates). Overlapping cells are generally identified as large single cells with irregular boundaries when analysis algorithms are applied to such images. As such, when the comparison of the cell perimeter and area is performed, the ratio falls well beyond the threshold for allowable variance from the ideal value, and the overlapping cells are excluded.

Figure 5:
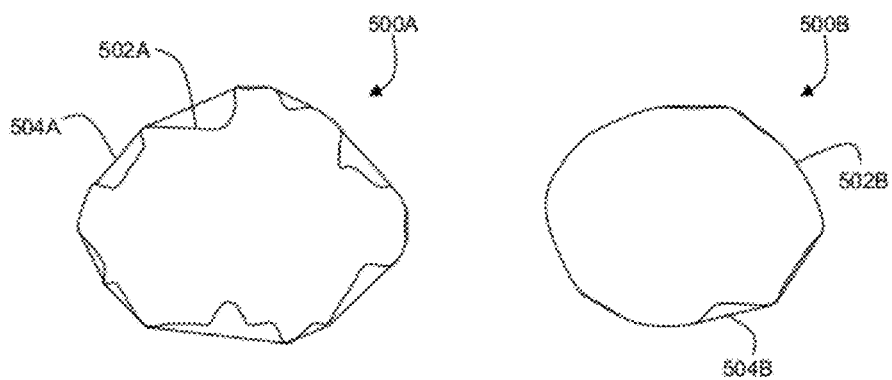
FIG. 5 is a schematic diagram showing two cells and convex hulls determined for each of the cells.

Another method for checking the shape of identified cells utilizes the convex hull of the polygonal representation of the cell outline described above and compares the area enclosed by the convex hull to the cell area determined from the image pixels. A high ratio of convex hull area to cell area can be used to identify irregularly shaped cells and exclude such cells from further analysis. FIG. 5 is a schematic diagram that includes two cells 500A and 500B. The perimeters of cells 500A and 500B are marked as 502A and 502B, respectively, in FIG. 5. A convex hull 504A is drawn around cell 500A, and a convex hull 504B is drawn around cell 500B. As shown in FIG. 5, the discrepancy between the convex hull area and the cell area is greater for cell 500A than for cell 500B. Given the high degree of irregularity for cell 500A, cell 500A can be excluded from the set of representative red blood cells.

In some embodiments, cell area measurements can be used in step 326 to exclude artifacts and overlapping cells from the set of representative blood cells. For example, only cells with an area ranging from 35 square microns to 65 square microns can be considered for red blood cell volume measurements. Imaged objects with an area less than 35 square microns are typically not red blood cells, but artifacts, such as a speck of dust in the sample. Similarly, imaged objects with an area greater than 65 square microns are typically not red blood cells; such object might correspond to a blob of stain or to several overlapping cells. While the foregoing example describes a 35 to 65 square micron area range, other ranges can be used to select red blood cells for measurement (e.g., 20 square microns to 80 square microns), and the range can be scaled based on the average cell size in the sample, thereby accounting for patient-to-patient variability. It has been determined experimentally that while the 35-to-65 square micron range can exclude some red blood cells, such range is more effective at removing artifacts from the sample image as compared to the 20-to-80 square micron range.

Optical density values can be used to select the set of representative red blood cells in the sample. For example, if the mean optical density value of an object imaged under blue light is too low, the object may be a white blood cell nucleus instead of a red blood cell. A mean optical density threshold can be used (e.g., mean optical density less than or equal to 0.33) for images acquired using blue light to exclude white blood cells from the set of representative red blood cells for the sample (e.g., a cell with a mean optical density less than or equal to 0.33 is likely to be a white blood cell). For images acquired under blue or yellow illumination, a mean optical density value for an object exceeding a certain threshold (e.g., mean optical density greater than or equal to 0.66) can be used to identify stacked, overlapping, and/or clustered red blood cells, which can be excluded from further analysis (e.g., a red blood cell with a mean optical density greater than or equal to 0.66 is likely to be overlapping another red blood cell).

The process shown in FIG. 3B terminates at step 328 with the final determination of a set of representative cells for further analysis.

(ii) Determining Image Features

The systems and methods disclosed herein use combinations of image features to calculate cellular volume and constituent values. The combinations typically include (but are not limited to) linear combinations of such image features that the inventors have discovered yield accurate, reproducible results for a wide variety of samples.

Figure 6:
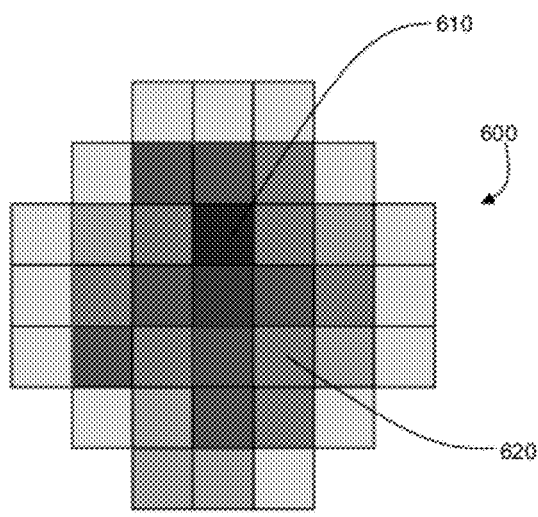
FIG. 6 is a schematic image of a cell showing variations in optical density among cell pixels.

Once a representative set of cells has been identified as described above, some or all of the features disclosed herein are calculated for each cell in the representative set based on one or more images of the cell obtained by system 100. A first set of features that can be calculated for each cell is the color-specific integrated optical density, IOD(c), which can be determined as follows:

$$IOD(c) = A \cdot OD_{mean}(c) \quad (3)$$

where A is the area of the cell, and $OD_{mean}(c)$ is the mean optical density of pixels in the cell when the cell is illuminated with light of color c. If images of a cell are obtained at different illumination wavelengths, a value of IOD(c) can be calculated for a cell at each illumination wavelength. FIG. 6 shows a schematic image, obtained with illumination light of color c, of a representative cell 600 identified through the process described in connection with flowchart 320 of FIG. 3B. The image of cell 600 includes a plurality of pixels. The mean optical density of pixels in cell 600, $OD_{mean}(c)$, corresponds to the sum of the pixel intensities in FIG. 6 divided by the number of pixels in the image.

A second set of features that can be calculated for each cell in the representative set is the color-specific volume of the cell, Vol(c). The volume of cell 600 in FIG. 6 is calculated by summing optical density values for each of the pixels that correspond to cell 600. First, the "height" of cell 600 at each pixel can be estimated as:

$$height = \frac{OD_{pixel}}{OD_{max}} \quad (4)$$

where $OD_{pixel}$ is the optical density associated with the given pixel, and $OD_{max}$ is the maximum optical density among all optical densities associated with the cell pixels. Thus, for example, pixel 620 in the image of cell 600 has an optical density that is smaller than the maximum optical density associated with pixel 610. The contribution of pixel 620 to the volume of cell 600 is the ratio $OD_{620}/OD_{max}$, where $OD_{620}$ is the optical density of pixel 620 and $OD_{max}$ is the optical density of pixel 610. Then, the cell volume, V, is calculated by summing the ratio of pixel optical density to maximum optical density for all pixels in cell 600:

$$V = \sum_{pixels} \frac{OD_{pixel}}{OD_{max}} = \frac{\sum_{pixels} OD_{pixel}}{OD_{max}} = \frac{N_{pixels} \cdot OD_{mean}}{OD_{max}} \quad (5)$$

where the sum of the optical densities associated with each of the pixels in cell 600 is replaced in Equation (5) by the product of the number of pixels in cell 600, $N_{pixels}$, and the mean pixel optical density for the pixels in cell 600, $OD_{mean}$.

Typically, the optical density for pixels near the edge of a cell is not a valid contributor to the volume measurement because light refracted at the edge of the cell creates an artificially dark border around the cell. To avoid this effect from such border pixels, the system can erode the mask at the cell periphery by one or more pixels as previously described, measure the mean optical density and the maximum optical density of the masked region of the cell, and, thereafter, extrapolate to the edge of the cell by multiplying by the area of the full, non-eroded mask.

Further, when multiple images corresponding to different illumination wavelengths are used to obtain images of a single cell, a cell volume calculation determination can be made at each color of illumination light. Accordingly, the color-specific cell volume can be determined as:

$$Vol(c) = \frac{A \cdot OD_{mean}(c)}{OD_{max}(c)} \quad (6)$$

where A is the area of the entire cell including the cell periphery, $OD_{mean}(c)$ is the color-specific mean optical density for pixels within the masked region of the cell, and $OD_{max}(c)$ is the color-specific maximum optical density for the eroded mask of the cell (e.g., pixel 610 in FIG. 6). The calculated color-specific cell volume Vol(c) can be scaled to express the cell volume in appropriate units (e.g., femtoliters).

In some embodiments, it is useful to add one or more correction factors to Equation (6) to adjust for the fact that some of the darkness of a cell image may not truly be due to the hemoglobin content of the cell. In addition, a scaling factor can be applied to convert the volume measurement to a unit of measurement such as femtoliters (fL). To account for these correction and scaling factors, Equation (6) can be rewritten as:

$$Vol(c) = \frac{S \cdot [A \cdot OD_{mean}(c)]}{OD_{max}(c) + C} + B \quad (7)$$

where S corresponds to a scaling factor or slope, C corresponds to a correction factor to account for bias in the determination of maximum optical density, and B corresponds to an intercept value that corresponds to a global offset value.

The correction factor, scaling factor, and intercept value can be determined experimentally using a data set of known volume values for multiple blood samples processed on, for example, a calibrated flow cytometer. A slightly different set of correction factors will, in general, provide the best result for each different sample, although correction factors can be determined based on the results across an entire data set. For example, for a data set containing known volume values for 1,000 blood samples, a correction factor that works best on average across the entire data set can be determined by selecting the correction factor that minimizes the sum of squared differences between measured and expected volume values across the entire data set. A scaling factor can be determined across the entire data set by selecting the scaling factor that best converts raw volume values to a desirable measurement unit such as femtoliters. The intercept value B can be selected for the data set to ensure that Equation (7) passes through the origin when the data are presented on a two-dimensional plot. The correction factor, scaling factor, and intercept value can be stored in a memory unit associated with electronic control system 108, and retrieved from memory when determining color-specific cell volumes as shown in Equation (7) for analysis of new samples.

Using Equation (3) and Equation (6) or (7), two features (e.g., integrated optical density IOD(c) and volume Vol(c)) can be determined for each color of illumination light used to obtain sample images. For example, if four different colors of illumination light are used, a total of eight different features can be determined for each cell in the representative set. In addition, as explained above, the area A of each individual cell can be determined from an image of the cell. The color-specific integrated optical densities and cell volumes, and the cellular area, can then be used to calculate metrics for each cell.

(iii) Calculation of Cellular Metrics

Cellular metrics such as cell volume and cellular constituent amounts can be calculated based on weighted combinations of some or all of the features calculated for representative cells disclosed above. In general, a metric M can be determined according to:

$$M = \sum_n [\omega_{n,i} \cdot IOD(n) + \omega_{n,v} \cdot Vol(n)] + \omega_a \cdot A + K \quad (8)$$

where n corresponds to each of the colors of illumination light used to obtain images of a representative cell, the $\omega_{n,i}$ values are color-specific weight coefficients for each of the color-specific integrated optical densities IOD(n), the $\omega_{n,v}$ values are color-specific weight coefficients for each of the color-specific volumes Vol(n), $\omega_a$ is a weight coefficient for the cell area A, and K is an offset value. For example, when four different illumination wavelengths are used to obtain images of cells (e.g., red=r, yellow=y, green=g, and blue=b), then the volume of a cell, V, can be determined as:

$$V = \omega_{r,i} \cdot IOD(r) + \omega_{y,i} \cdot IOD(y) + \omega_{g,i} \cdot IOD(g) + \omega_{b,i} \cdot IOD(b) + \quad (9)$$
$$\omega_{r,v} \cdot Vol(r) + \omega_{y,v} \cdot Vol(y) + \omega_{g,v} \cdot Vol(g) + \omega_{b,v} \cdot Vol(b) + \omega_a \cdot A + K$$

Amounts of cellular constituents can be determined in similar fashion. For example, a concentration of hemoglobin in a cell, H, can be calculated according to:

$$H = \omega_{r,i} \cdot IOD(r) + \omega_{y,i} \cdot IOD(y) + \quad (10)$$
$$\omega_{g,i} \cdot IOD(g) + \omega_{b,i} \cdot IOD(b) + \omega_{r,v} \cdot Vol(r) +$$
$$\omega_{y,v} \cdot Vol(y) + \omega_{g,v} \cdot Vol(g) + \omega_{b,v} \cdot Vol(b) + \omega_a \cdot A + K$$

The difference between Equations (9) and (10) above is in the values of the weight coefficients and the offset K. Using Equations (9) and (10), cell volumes and constituent amounts (e.g., the amount of hemoglobin) can be determined for multiple cells in the sample. The results can be averaged to determine mean cell volume and mean concentrations of constituents (e.g., mean cell hemoglobin) for the sample. The determination of cell volumes and the amount of cellular constituents based on weighted combinations of color-specific image features and cell area has been observed to significantly improve the accuracy of such measurements, as compared to volume and constituent measurements based on single-color optical density values and cell area.

The weight coefficients associated with the color-specific features in Equation (8) can be determined based on available training data, for example, by determining linear regression coefficients that map the experimentally determined sample features onto training data comprising known volume and/or constituent concentration values for such samples. Using a linear regression approach to determine color-specific weights can improve the accuracy of sample mean cell volume and mean constituent concentration measurements by correcting for uncontrollable factors that impact the volume measurement such as cell-to-cell variability in membrane thickness and stain absorption. After color-specific weight values have been determined from training data, the weight values can be stored and later retrieved from a storage unit (e.g., an electronic memory unit) prior to analysis of each sample.

In general, a wide variety of different samples can be used to determine appropriate weight coefficients. To obtain highly reproducible results, it can be advantageous to use training data that span the entire range of values of quantities that are calculated. Further, if samples to be analyzed include unusual morphological features such as cell clumps, it can be advantageous to use training data that include representative samples of such features.

As an example, after determining a set of weight coefficients from a set of training data for the determination of cell volume, Equation (9) can be re-written as follows:

$$V = (-4.04) + IOD(r) + 8.49 \cdot IOD(y) + (-3.69) \cdot IOD(g) + \quad (11)$$
$$4.40 \cdot IOD(b) + 4.68 \cdot Vol(r) + (-8.20) \cdot Vol(y) +$$
$$3.57 \cdot Vol(g) + 0.0159 \cdot Vol(b) + (-0.0125) A + 4.84$$

Similarly, after determining suitable weight coefficients from a set of training data for the determination of cell hemoglobin, Equation (10) can be re-written as:

$$H = (-1.05) + IOD(r) + (-2.44) \cdot IOD(y) + 1.12 \cdot IOD(g) + \quad (12)$$
$$2.15 \cdot IOD(b) + 1.95 \cdot Vol(r) + (-0.112) \cdot Vol(y) +$$
$$(-1.27) \cdot Vol(g) + 0.457 \cdot Vol(b) + (-0.221) \cdot A + -5.73$$

The systems and methods disclosed herein can be used to analyze both whole blood samples (e.g., samples taken from patients) and quality control compositions. The weight coefficients shown in Equations (9)-(12) can be used to analyze both whole blood samples and quality control compositions. Quality control compositions typically include various types of preserved mammalian blood cells, and are designed to mimic whole blood samples when processed on an automated hematology system.

Quality control compositions can be analyzed to assess the operating condition of a blood analysis device such as an automated hematology system that embodies and executes the methods disclosed herein. For example, to perform an assessment of a device, the device can be used to analyze one or more control compositions multiple times. The analysis results (e.g., the determination of quantities such as cell hemoglobin, cell volume, mean cell hemoglobin, and mean cell volume) from repeated analysis of the same control compositions can be compared to assess the linearity of the results produced by the device.

In some embodiments, a device can be used to analyze control compositions to assess the accuracy of the results produced by the device. For example, results from analysis of control compositions by the device (e.g., the determination of quantities such as cell hemoglobin, cell volume, mean cell hemoglobin, and mean cell volume) can be compared to reference values of these quantities for the control compositions to assess the device's accuracy. If a difference between the determined and reference values for one or more of these quantities exceeds a threshold value, the device can be re-calibrated. Re-calibration can include, for example, re-determining values of some or all of the weight coefficients in Equations (9)-(12) from reference blood samples, as described herein.

In Equations (9)-(12), four colors of illumination light (red, yellow, green, and blue) are used to illuminate the sample, and integrated optical densities and cell volumes are calculated from images that correspond to each of these colors. The illumination wavelengths used to calculate the color-specific integrated optical density values and volumes can be, e.g., 635 nm, 598 nm, 525 nm, and 415 nm, although other values within the red, yellow, green, and blue regions of the electromagnetic spectrum can be used in other embodiments. More generally, different numbers of illumination wavelengths can be used, and images corresponding to each of the illumination wavelengths can be obtained and used to calculate color-specific values of integrated optical density and/or cell volume. For example, in some embodiments, three different wavelengths of light are used to illuminate a sample. In certain embodiments, more than four wavelengths (e.g., five wavelengths, six wavelengths, seven wavelengths, eight wavelengths, ten) of illumination light can be used, and color-specific integrated optical densities, cell volumes, and weight coefficients can be determined at some or all of the illumination wavelengths. In general, the wavelengths of illumination light can be selected such that images at each of the different wavelengths include different information about the sample. For example, if the sample includes three spectral contributors, three wavelengths of illumination light can be selected for use such that each of the three wavelengths is most strongly absorbed by a different one of the spectral contributors.

As discussed above, color-specific weight coefficients in Equation (8) can be determined by mapping linear regression coefficients for experimentally determined features for a large number (e.g., 1,000) of blood samples onto a training data set comprising known values of cell volume and/or concentrations of various cellular constituents for such samples, obtained for example from a calibrated flow cytometry system. With changes to sample preparation parameters (e.g., modifications to stain compositions affecting the appearance of stained cells or other factors impacting how cells absorb stain such as the extent of sample drying before fixing and staining), the process of determining color-specific weights and an intercept value for Equation 8 can be repeated to ensure determination of accurate volume and cell constituent measurement values for a given set of sample preparation parameters. However, once sample preparation parameters have been optimized for a particular sample preparation system, the experimentally derived weight coefficients and other parameter values in Equation (8) will generate accurate and reproducible measurements of cell volume and/or cell constituent amounts.

In Equation (8), metric M is calculated as a weighted linear combination of the color-specific integrated optical densities, the color-specific volumes, and the cell area. Not all of these features are used to determine values of metrics in all embodiments, however. For example, in some embodiments, a metric M can be calculated as a weighted combination of only the color-specific integrated optical densities or the color-specific volumes. In certain embodiments, a metric M can be calculated as a weighted combination of the cell area and either the color-specific integrated optical densities or the color-specific volumes. In some embodiments, a metric M can be calculated as a weighted linear combination of the color-specific integrated optical densities and the color-specific volumes. In general, a suitable combination of features used to calculate a particular metric M can be determined using reference samples for which values of the metric M are known.

When determining the amount of a particular constituent in sample cells, if only a single spectral contributor is present in the sample (e.g., an absorptive contributor such as hemoglobin), than the total amount of that contributor present in a particular cell can be determined by summing intensity contributions from each of the pixels in the image that correspond to the selected cell. As the intensity contributions correspond only to absorption by hemoglobin, only one sample image would be needed to determine the total amount of hemoglobin present in the cell.

In practice, however, samples are typically prepared with one or more stains to assist a technologist or an automated imaging system to identify, count and classify various cell types. With multiple spectral contributors in the sample, the absorption at each illumination wavelength is a combination of absorption due to each contributor in the sample; the total contribution at any wavelength for a particular cell still corresponds to the sum of contributions at that wavelength from each of the pixels representing the cell. Thus, with spectral contributors hemoglobin (H), eosin (E), and azure (A) present in the sample, and assuming that three images of the sample correspond to illumination light having central wavelengths in the yellow (y), green (g), and blue (b) regions of the electromagnetic spectrum, the optical densities OD at each of these three wavelengths for a particular cell (or for all pixels in the image that correspond to one or more cells) can be assumed to be a linear combination of the absorption due to each of the spectral constituents at each wavelength:

$$OD(y) = H \cdot \alpha_{y,H} + E \cdot \alpha_{y,E} + A \cdot \alpha_{y,A}$$

$$OD(g) = H \cdot \alpha_{g,H} + E \cdot \alpha_{g,E} + A \cdot \alpha_{g,A}$$

$$OD(b) = H \cdot \alpha_{b,H} + E \cdot \alpha_{b,E} + A \cdot \alpha_{b,A} \qquad (13)$$

where $\alpha_{i,j}$ is the absorption coefficient for spectral contributor j (e.g., hemoglobin H, eosin E, or azure A) at wavelength i (e.g., yellow y, green g, or blue b).

Each of the central wavelengths of light can be determined by passing a known spectrum of light through the sample to the detector and measuring the absorbance of the sample. For example, the detector can acquire three images of the sample using an illumination source with narrow illumination spectra in the yellow, green, and blue regions, respectively. Where each spectral contributor has an absorption spectrum containing a local maximum, illumination sources can be selected such that the emission spectra correspond to or best approximate the spectral contributor local maxima. For example, the blue illumination can be selected as the wavelength that corresponds to the peak absorbance of hemoglobin in the sample (e.g., 415 nm). The yellow illumination can be correlated to the wavelength that corresponds to the peak absorbance of azure stain in the sample (e.g., 598 nm). Similarly, the green illumination wavelength can be selected at the wavelength that corresponds to the peak absorbance of eosin stain in the sample (e.g., 525 nm). Additional illumination wavelengths can be selected to correlate with peak absorbance values for additional spectral contributors in the sample.

The optical density quantities OD(y), OD(g), and OD(b) can be determined from the image information, and the absorption coefficients $\alpha_{i,j}$ can be obtained from literature sources or determined experimentally. Thus, the system of Equation (13) includes three unknowns—H, E, and A—and can be solved to yield the amounts of each of these three spectral contributors present in each particular cell, or collectively for all cells in the sample if the pixels selected for analysis collectively correspond to all of the identified cells in the images.

Nonetheless, the methods and systems disclosed herein present a simpler, more efficient method for determining amounts of cellular constituents. As shown above, Equation (8)—with suitable weight coefficients—can be used to determine constituent amounts of only those constituents of interest, increasing the speed with which sample analysis can be completed. Further, in complex samples where the number of spectral contributors is not well known, it can be difficult to construct a system of equations such as in Equation (13). Equation (8), however, permits amounts of specific cellular constituents to be determined even if the presence of other spectral contributors in the cell is not well established. Thus, while in some embodiments the spectral contributions from hemoglobin, eosin, and azure in the system of Equation (13) can be distinguished by obtaining images at three different illumination wavelengths, using more than three features and/or more than three illumination wavelengths as described herein to determine values of cell metrics such as cell hemoglobin, cell volume, mean cell hemoglobin, and mean cell volume permits correction for other systematic and non-systematic sources of error when measuring blood samples.

In addition to color-specific integrated optical densities and volumes, and cell area, other image features can be used to determine cell volumes and/or amounts of cellular constituents. In some embodiments, for example, Equation (8) can include an extra term that corresponds to the product of a cell's perimeter and a weigh coefficient. An appropriate weighting factor can be determined for the cell perimeter term from training data, as described above. More generally, a variety of additional terms derived from cell images, with suitable weight coefficients determined from training data, can be included in Equation (8). Such terms can include geometrical image features relating to the morphology of the cells and/or color-specific measurements of integrated optical density and volume at more than three or four illumination wavelengths. Without wishing to be bound by theory, the additional terms may allow the fitting—which is performed simultaneously on reference sample information to determine values of all weighting factors—to correct for effects such as imaging aberrations, absorption from other sample components, and systemic measurement errors, that are not fully accounted for by the model of Equation (8). For example, it has been found that the inclusion of integrated optical density and cell volume terms corresponding to a red illumination wavelength and a term corresponding to cell area improves the accuracy of determination of cell hemoglobin in many samples as compared to measurement techniques that do not use sample images acquired at a red illumination wavelength or cell area measurements.

In general, the methods and systems disclosed herein can be used to determine amounts of naturally present constituents in samples (e.g., hemoglobin in red blood cells) and/or amounts of constituents that have been added to samples (e.g., stains that have been applied, and that bind to cellular components). Further, in some embodiments, the methods and systems disclosed herein can be used to determine the amounts of more than one constituent present in the sample. For example, by applying suitable stains and/or selecting appropriate central wavelengths for the sample images, amounts of two or more constituents can be determined. Consider a sample that includes hemoglobin as a naturally-occurring absorbing constituent. The sample can be stained with two broadly absorptive stains $S(1)$ and $S(2)$, and with a third stain $S(3)$ with a relatively narrow absorption band. $S(3)$ selectively binds to a particular constituent of interest in cells such that measuring the amount of $S(3)$ present yields a measurement of the constituent.

If the absorption spectra of hemoglobin and $S(3)$ are sufficiently separated spectrally such that hemoglobin has significant absorption at only wavelengths $\lambda_1, \lambda_2,$ and $\lambda_3$ but not at $\lambda_4$, and $S(3)$ has significant absorption at only wavelengths $\lambda_2, \lambda_3,$ and $\lambda_4$ but not at $\lambda_1$, then assuming $S(1)$ and $S(2)$ have significant absorption at all four wavelengths, the amount of cellular hemoglobin can be determined according to the methods disclosed herein for measuring cell constituent amounts from images of the sample corresponding to illumination wavelengths $\lambda_1, \lambda_2,$ and $\lambda_3$, and the amount of $S(3)$ can be determined according to the same methods from images of the sample corresponding to illumination wavelengths $\lambda_2, \lambda_3,$ and $\lambda_4$. These approaches can be generalized further to larger numbers of constituents of interest, and larger or smaller numbers of broadly absorptive spectral contributors such as $S(1)$ and $S(2)$.

Reporting of Results

In certain embodiments, the determined cell volumes, constituent amounts, mean cell volume, and mean constituent concentrations can be displayed to a system operator using, e.g., display 110. The results can be displayed on a per cell basis, or as averaged results for the whole sample. Also, calculated numerical results (e.g., for individual cells) can be overlaid atop one or more images of the cells. In general, a system operator can exercise control over the manner in which results are displayed using human interface unit 112 (e.g., a keyboard and/or mouse and/or any other input device). The system operator can also exercise control over any of the other parameters, conditions, and options associated with the methods disclosed herein through interface unit 112 and display 110.

One or more metrics can also be calculated from the mean cell volume and/or mean cell hemoglobin measurements, and displayed on display 110. In some embodiments, for example, red blood cell distribution width can be calculated and displayed for a human operator. In turn, the red cell distribution width can be used to calculate and display the possibility of anisocytosis and/or anemia. In addition, mean cell hemoglobin measurements can be used with a hematocrit value for the sample to calculate mean cell hemoglobin concentration.

Cell volume and constituent concentration measurements and/or metrics calculated therefrom can be stored along with sample images in an electronic storage unit associated with control system 108. For example, this information can be stored in an electronic record associated with the patient to whom sample 104 corresponds. Alternatively, or in addition, the information can be transmitted to one or more physicians or other treatment personnel. The information can be transmitted via a network (e.g., a computer network) to a computing device. Further, the information can be transmitted to a handheld device such as a mobile phone, and the transmission can include an alert or warning if the metrics fall outside a predetermined range of values.

Other Analytes

As explained above, this disclosure focuses for illustrative purposes on the determination of cell volume and cell constituent amounts in red blood cells. However, the systems and methods disclosed herein can also determine volumes and cell constituent amounts for other types of cells. In particular, Equation (8) can be used to determine values of cellular metrics for a variety of different types of cells.

As an example, the systems and methods disclosed herein can use a linear combination of color-specific optical density and volume measurements—with suitably determined weight coefficients—to compute a platelet volume for platelets within a given blood sample. Measurements of platelet volume within a sample can be averaged to yield a measurement of mean platelet volume. As with the previously described example for calculating cell volume and constituent amounts in red blood cells, images of the blood sample are acquired using multiple wavelengths of light. The sample images are then analyzed according to the steps in flow chart 300 of FIG. 3A to yield measurements of platelet volumes.

Figure 9A:
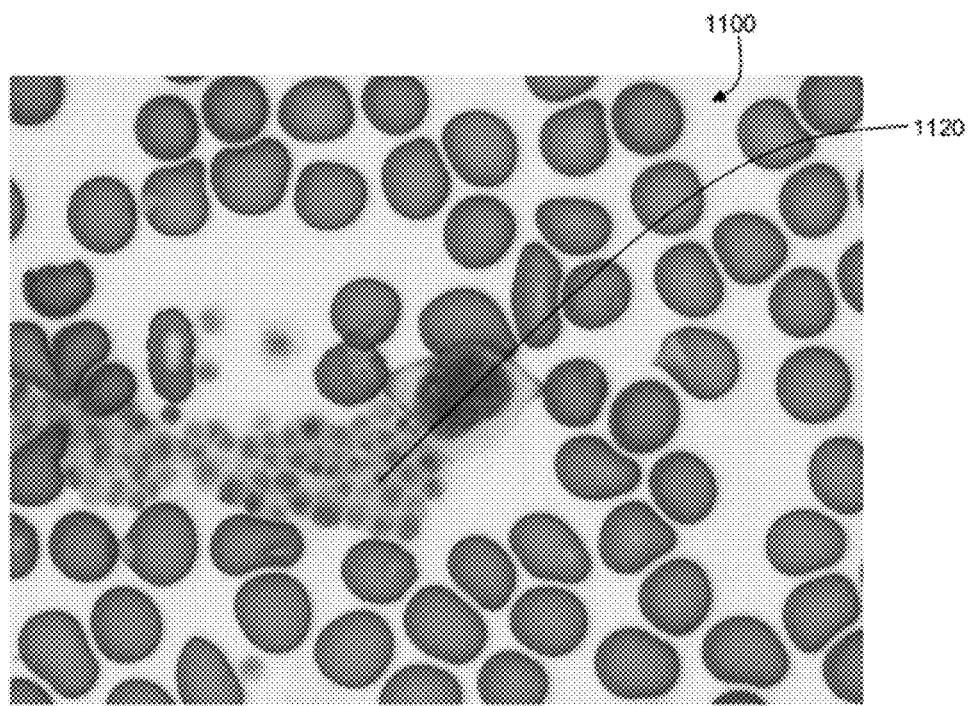
FIGS. 9A and 9B are images of a blood sample.
Figure 9B:
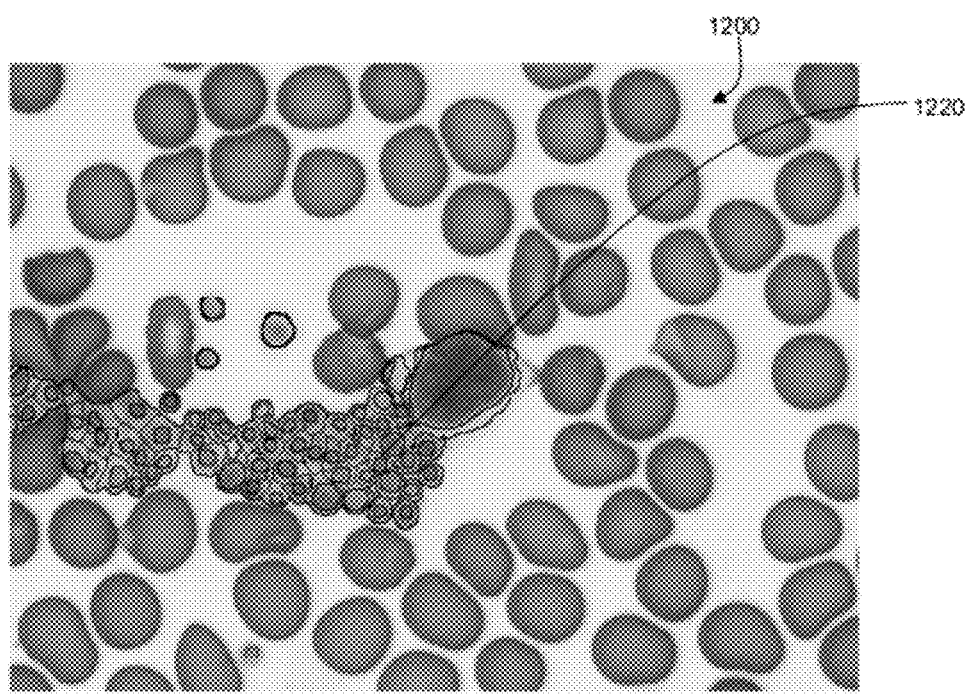

The first step in flow chart 300 is the selection of a set of representative platelets in step 302. An example of a prepared blood sample containing platelets is illustrated in FIGS. 9A and 9B. FIG. 9A shows an image 1100 of a specimen of blood that includes a large cluster or clump of platelets 1120. As platelets can clump and form a packed cluster, additional image processing may be required to identify the individual platelets within a clump or cluster for possible inclusion in the set of representative platelets. An example of such processing is illustrated in FIG. 9B. Objects in the image are segmented to identify individual platelets within the cluster. As shown in the segmented cluster 1220 of FIG. 9B, the individual platelets are identified by borders.

The segmentation process can proceed in three stages. In a first stage, central regions of the individual platelets are identified in each image. Platelet central regions are shown as the nearly-circular regions in FIG. 9B. The platelet central regions appear as the darkest regions of the platelets.

In the second stage, pixels in the image that may be part of a platelet are identified. Pixels can be determined as being part of a platelet based on one or more threshold conditions on the value of a given pixel. In some embodiments, if the intensity value of a pixel is greater than 120 in an image acquired at a blue illumination wavelength (e.g., 415 nm), and the intensity value is also at least 30 levels higher than an intensity value of the same pixel in an image acquired at a green illumination wavelength (e.g., 525 nm), the pixel is identified as being part of a platelet.

In the third stage, each of the pixels identified in the second stage as being part of a platelet is assigned to a platelet corresponding to the platelet center that is nearest to the pixel. If the distance between a particular pixel and its nearest platelet center exceeds a threshold value, the pixel is not assigned to any platelet. This stage results in assignment of a set of pixels corresponding to each of the identified platelets. Sets of pixels corresponding individual platelets are depicted in FIG. 9B as irregularly encircling platelet central regions.

In some embodiments, the boundaries between platelets can be subjected to morphological operations such as dilation. Dilation can be halted, for example, when platelet boundaries do not overlap. However, erosion of the pixel mask (e.g., the subset of pixels) corresponding to each platelet is typically not performed as described above in connection with red blood cells. Platelet boundaries are typically thinner and less refractive than those of red blood cells. As a result, platelet boundaries do not appear dark in images, in contrast to the appearance of red blood cells, and typically erosion of the pixel masks corresponding to individual platelets is not performed. With platelet boundaries identified and pixels assigned to a given platelet, the area of each platelet within the representative set can be calculated.

In general, a variety of segmentation algorithms can be used to segment a cluster of platelets into individual platelets. Examples of such algorithms are described in U.S. Pat. Nos. 7,689,038 and 7,881,532, the entire contents of each of which are incorporated herein by reference.

As described above in connection with red blood cells, additional steps can also be performed to determine whether individual platelets should be included in the set of representative platelets used in subsequent calculations. Platelets that touch any of the edges of the images or are otherwise obscured in the images are removed from the set of representative platelets and not used in further calculations.

Applying integrated optical density thresholds can further refine the set of representative platelets. For example, platelets with an integrated optical density value greater than 600 when illuminated with light at a yellow illumination wavelength can be excluded from the representative platelet set; such objects are typically bigger than a platelet and are often red blood cells. In addition, platelets with an integrated optical density value greater than 200 when illuminated with light at a blue illumination wavelength can be excluded from the representative platelet set; such objects are typically too dark to be a platelet and often indicate dust or other debris in the sample.

In some embodiments, a classifier such as a linear discriminant classifier is applied to identify platelets that have settled on top of red blood cells within the sample. The classifier utilizes a combination of multiple platelet candidate features (e.g., five or more, ten or more, fifteen or more, etc.) relating to the shape, texture, and color of platelet candidates to identify and exclude overlapped platelets from the set of representative platelets.

Next, in step 304, color-specific integrated optical density and volume values for the set of representative platelets are determined according to Equations (3) and (6) or (7). Then, in step 306, platelet metrics such as platelet volume are calculated using the features determined in step 304 according to Equation (8). As described above, the weights associated with the features can be determined based on training data, for example, by determining linear regression coefficients that map the features onto training data comprising known platelet volume values for multiple blood samples (e.g., as reported by a calibrated flow cytometry system).

As an example, after determining a set of weight coefficients from a set of training data for the determination of cell volume, Equation (9) can be re-written so that platelet volume (PV) can be determined as follows:

$$PV = (-0.0047) \cdot IOD(y) + \\ 0.050 \cdot IOD(g) + 0.082 \cdot IOD(b) + 0.28 \cdot Vol(y) + \\ (-0.15) \cdot Vol(g) + (-0.031) \cdot Vol(b) + (-0.058) \: A + 4.0 \tag{14}$$

As discussed above, the systems and methods disclosed herein can be used to analyze both whole blood samples (e.g., samples taken from patients) and quality control compositions. The weight coefficients shown in Equation (9) and (14) can be used to analyze both whole blood samples and quality control compositions. Quality control compositions can be analyzed to assess the operating condition of a blood analysis device such as an automated hematology system that embodies and executes the methods disclosed herein. For example, to perform an assessment of a device, the device can be used to analyze one or more control compositions multiple times. The analysis results (e.g., the determination of quantities such as platelet volume and mean platelet volume) from repeated analysis of the same control compositions can be compared to assess the linearity and/or accuracy of the results produced by the device, and can be used to determine whether re-calibration of the device is warranted.

Platelet volumes can be determined for all platelets within one or more sets of representative platelets to calculate a mean platelet volume (MPV) value for the sample. While other illumination wavelengths in the electromagnetic spectrum are useful for calculating platelet volumes, the inventors have found that including color-specific features for platelets imaged with a red illumination wavelength in Equation (8) did not significantly increase the accuracy of calculating platelet volumes or sample MPV values.

The systems and methods disclosed herein can also be used to determine other cellular metrics for platelets. In particular, the systems and methods can be used to determine amounts of constituents in platelets using Equation (8) with weight coefficients determined from reference samples, as described above.

Automated Sample Preparation Systems

Figure 10:
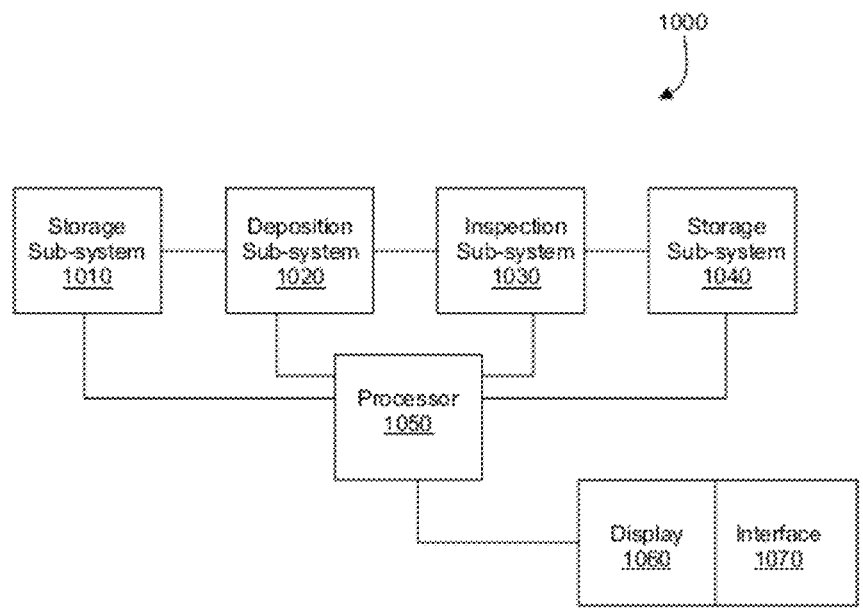
FIG. 10 is a schematic diagram of an automated sample processing system.

The systems and methods disclosed herein can be used with a variety of different automated sample preparation systems. FIG. 10 shows a schematic diagram of an embodiment of an automated sample preparation system 1000. System 1000 includes multiple sub-systems for storing substrates, depositing samples on substrates, inspecting samples prepared on substrates, and storing prepared samples.

Substrate storage sub-system 1010 is configured to store substrates prior to the deposition of samples thereon. Substrates can include, for example, microscope slides, coverslips, and similar planar, optically transparent substrates. The substrates can be formed from a variety of different amorphous or crystalline materials including various types of glasses. Sub-system 1010 can include a manipulator that selects individual substrates from a storage container and transfers the selected substrates to sample deposition sub-system 1020.

Sample deposition sub-system 1020 deposits a selected quantity of a sample of interest—such as a blood sample—onto a substrate. Sub-system 1020 includes, in general, a variety of fluid transfer components (e.g., pumps, fluid tubes, valves) configured to deposit the sample. The fluid transfer components can also be configured to expose the substrate to solutions of various types, including wash solutions, one or more stains that bind to the sample, fixing solutions, and buffer solutions. Sub-system 1020 can also feature fluid removal components (e.g., a vacuum sub-system) and a drying apparatus to ensure that the sample is fixed to the substrate. A substrate manipulator can transfer the substrate supporting the sample to imaging sub-system 1030.

Inspection sub-system 1030 includes various components for obtaining images of samples on substrates, and for analyzing the images to determine information about the samples. For example, inspection sub-system 1030 can include one or more light sources (e.g., light emitting diodes, laser diodes, and/or lasers) for directing incident light to a sample. Imaging sub-system 1030 can also include an optical apparatus (e.g., a microscope objective) for capturing transmitted and/or reflected light from a sample. A detector (e.g., a CCD detector) coupled to the optical apparatus can be configured to capture images of the sample. Information derived from analysis of the images of the sample can be stored on a variety of optical and/or electronic storage media for later retrieval and/or further analysis.

Following inspection, a substrate manipulator can transfer the substrate to storage sub-system 1040. Storage sub-system 1040 can label individual substrates, for example, with information relating to the source of the sample applied to the substrate, the time of analysis, and/or any irregularities identified during analysis. Storage sub-system can also store processed substrates in multi-substrate racks, which can be removed from system 1000 as they are filled with substrates.

As shown in FIG. 10, each of the various sub-systems of system 1000 can be linked to a common electronic processor 1050. Processor 1050 can be configured to control the operation of each of the sub-systems of system 1000 in automated fashion, with relatively little (or no) input from a system operator. Results from the analysis of samples can be displayed on system display 1060 for a supervising operator. Interface 1070 permits the operator to issue commands to system 1000 and to manually review the automated analysis results.

Additional aspects and features of automated sample processing systems are disclosed, for example, in U.S. patent application Ser. No. 12/943,687, filed on Nov. 10, 2010, the entire contents of which are incorporated herein by reference.

Hardware and Software Implementation

The method steps and procedures described herein can be implemented in hardware or in software, or in a combination of both. In particular, electronic processor 114 can include software and/or hardware instructions to perform any of the methods discussed above. The methods can be implemented in computer programs using standard programming techniques following the method steps and figures disclosed herein. Program code is applied to input data to perform the functions described herein. The output information is applied to one or more output devices such as a printer, or a display device, or a web page on a computer monitor with access to a website, e.g., for remote monitoring.

Each program is preferably implemented in a high level procedural or object oriented programming language to communicate with a processor. However, the programs can be implemented in assembly or machine language, if desired. In any case, the language can be a compiled or interpreted language. Each computer program can be stored on a storage medium or device (e.g., an electronic memory) readable by the processor, for configuring and operating the processor to perform the procedures described herein.

Figure 11:
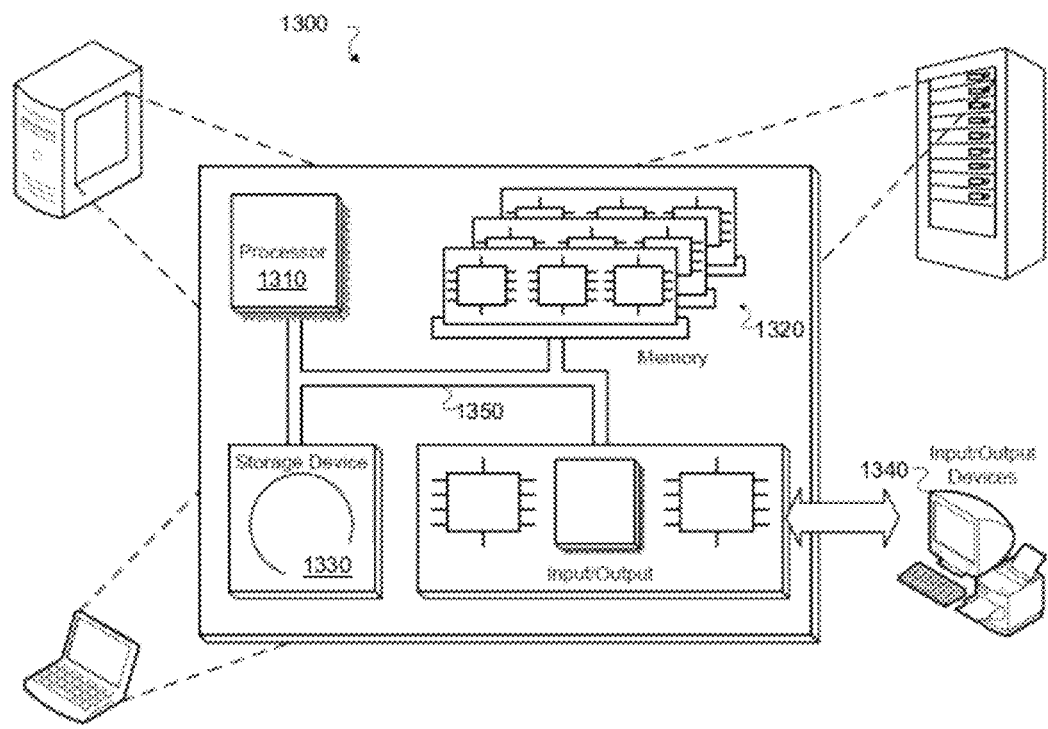
FIG. 11 is a schematic diagram of a computing system for measuring volume and constituents of cells.

FIG. 11 is a schematic diagram of a computer system 1300 that can be used to control the operations described in association with any of the computer-implemented methods described herein, according to one embodiment. The system 1300 includes a processor 1310, a memory 1320, a storage device 1330, and an input/output device 1340. Each of the components 1310, 1320, 1330, and 1340 are interconnected using a system bus 1350. The processor 1310 is capable of processing instructions for execution within the system 1300. In one embodiment, the processor 1310 is a single-threaded processor. In another embodiment, the processor 1310 is a multi-threaded processor. The processor 1310 is capable of processing instructions stored in the memory 1320 or on the storage device 1330 to display graphical information for a user interface on the input/output device 1340. The processor 1310 can be substantially similar to the processor 1050 described above with reference to FIG. 10.

The memory 1320 stores information within the system 1300. In some embodiments, the memory 1320 is a computer-readable medium. The memory 1320 can include volatile memory and/or non-volatile memory.

The storage device 1330 is capable of providing mass storage for the system 1300. In general, the storage device 1330 can include any non-transitory tangible media configured to store computer readable instructions. In one embodiment, the storage device 1330 is a computer-readable medium. In various different embodiments, the storage device 1330 may be a floppy disk device, a hard disk device, an optical disk device, or a tape device.

The input/output device 1340 provides input/output operations for the system 1300. In some embodiments, the input/output device 1340 includes a keyboard and/or pointing device. In some embodiments, the input/output device 1340 includes a display unit for displaying graphical user interfaces. In some embodiments, the input/output device 1340 includes one or more of the display 1060 and interface 1070 described above with reference to FIG. 10.

The features described can be implemented in digital electronic circuitry, or in computer hardware, firmware, or in combinations of them. The features can be implemented in a computer program product tangibly embodied in an information carrier, e.g., in a machine-readable storage device, for execution by a programmable processor; and features can be performed by a programmable processor executing a program of instructions to perform functions of the described embodiments by operating on input data and generating output. The described features can be implemented in one or more computer programs that are executable on a programmable system including at least one programmable processor coupled to receive data and instructions from, and to transmit data and instructions to, a data storage system, at least one input device, and at least one output device. A computer program includes a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Various software architectures can be used for implementing the methods and systems described in this application. For example, a publish/subscribe messaging pattern can be used in implementing the methods and systems described herein. In the case of publish/subscribe messaging, the system includes several hardware and software modules that communicate only via a messaging module. Each module can be configured to perform a specific function. For example, the system can include one or more of a hardware module, a camera module, and a focus module. The hardware module can send commands to the imaging hardware implementing auto-focus functions, which in turn triggers a camera to acquire images. In some embodiments, the hardware module can include the control system 108 described above with reference to FIG. 2.

A camera module can receive images from the camera and determine camera parameters such as shutter time or focus. Images can also be buffered in the computer's memory before being processed by the camera module. When performing the initial search for the tilt of the slide, the camera module can also send a message interrupting the hardware module when it has seen enough images to determine the proper shutter time or focus. In some embodiments, the camera module includes the detector 106 described above with reference to FIG. 2.

The system can also include a focus module that can be implemented as software, hardware or a combination of software and hardware. In some embodiments, the focus module examines all the frames in a stack and estimates how far the stack is from the ideal or ideal focal distance. The focus module can also be responsible for assigning a focus score to each frame in a stack of images.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. Computers include a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer. Alternatively, the computer can have no keyboard, mouse, or monitor attached and can be controlled remotely by another computer The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network, such as the described one. The relationship of client and server arises by virtue of computer programs running on the respective computers and having a client-server relationship to each other.

The processor 1310 carries out instructions related to a computer program. The processor 1310 can include hardware such as logic gates, adders, multipliers and counters. The processor 1310 can further include a separate arithmetic logic unit (ALU) that performs arithmetic and logical operations.

Other Embodiments

It is to be understood that the foregoing description is intended to illustrate and not limit the scope of the disclosure, which is defined by the scope of the appended claims. Other aspects, advantages, and modifications are within the scope of the following claims. For example, although the foregoing description and the schematic diagram in FIG. 2 discuss the measurement of transmitted light from a sample, the methods and systems disclosed herein can also be used when images of the sample correspond to light reflected from the sample. Certain samples may be naturally reflective, or can be tagged with reflective markers, such that reflected light provides a convenient method for determining amounts of cellular constituents and/or volume. In some embodiments, sample 104 can be positioned atop a substrate such as a microscope slide with a reflective coating. The reflective coating can function to direct once-transmitted light back through the sample a second time, so that the measured "reflected" light actually corresponds to incident light that has twice been transmitted through the sample.

In general, the methods and systems disclosed herein can be used to determine per-cell volumes, constituent content, and/or sample mean cell volume or mean cell constituent content for a variety of different sample types. For example, cell volumes and constituent contents such as hemoglobin or other proteins can be determined for samples that include cells from body fluids and tissues, including blood, bone marrow, urine, epithelial tissue, tumors, semen, spittle, and other tissues or circulating or non-circulating biological fluids.

EXAMPLES

Example 1

To evaluate the effectiveness of the systems and methods disclosed herein for determining a mean cell volume for a blood sample, a 1 µL sample of blood was deposited on a microscope slide to form a monolayer of red blood cells on the slide. The blood sample was deposited using the system disclosed in co-pending U.S. patent application Ser. No. 12/430,885, the entire contents of which are incorporated herein by reference. The sample was then prepared using fixative, red stain (e.g., comprising eosin Y), blue stain (e.g., comprising azure B and methylene blue), and rinse formulations disclosed in co-pending U.S. Patent Application Ser. No. 61/505,011 in an automated system of the type disclosed in co-pending U.S. patent application Ser. No. 13/293,050, the entire contents of which are incorporated herein by reference. After the blood sample was fixed, stained, rinsed, and dried, an automated transport mechanism loaded the slide onto an automated stage at a low magnification (e.g., under a 10× objective lens) imaging station.

The automated transport mechanism positioned the sample between a light source (e.g., source 106) and a detector (e.g., detector 102). High magnification images of the sample were acquired at locations corresponding to objects of interest. The detector was paired with a 50× objective lens and included a 640-by-480 pixel CCD sensor. The pixel size for images acquired via the detector was 7.4 µm; the dimensions of the field of view were:

$$\text{width} = \left(640 \text{ pixels} \cdot 7.4 \frac{\mu m}{\text{pixel}}\right)/50 = 95 \text{ } \mu m$$

$$\text{height} = \left(480 \text{ pixels} \cdot 7.4 \frac{\mu m}{\text{pixel}}\right)/50 = 71 \text{ } \mu m$$

Figure 7:
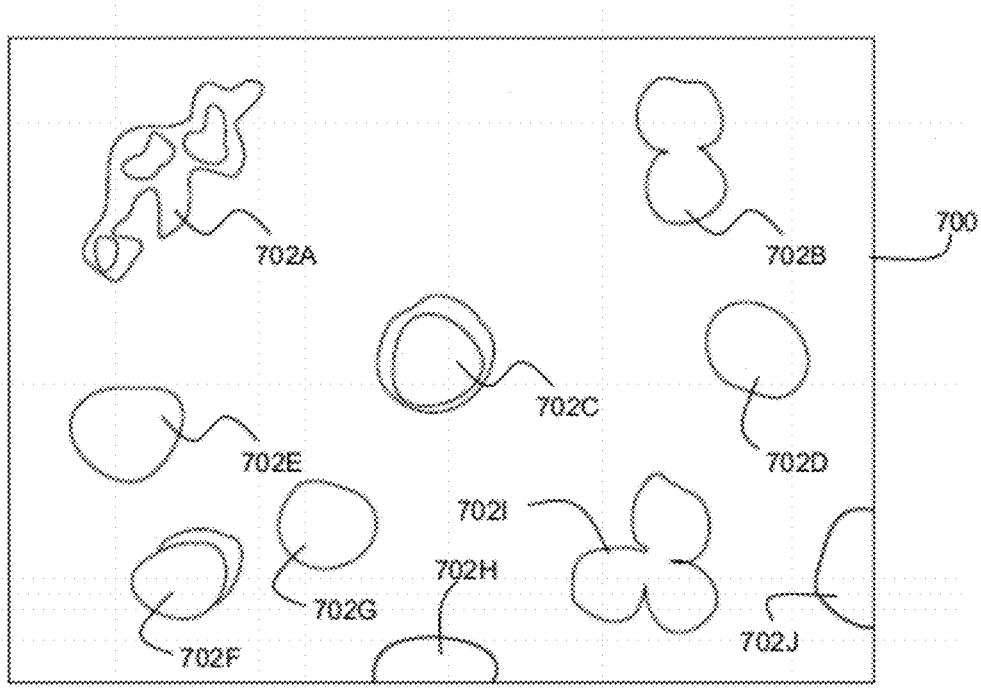
FIG. 7 is a schematic image of a blood sample.

The imaging system acquired several hundred images of the sample using the 50× objective lens. For each location on the sample, images were acquired at four different colors of illumination light (635, 598, 525, and 415 nm). Each image typically included 100 or more red blood cells and therefore, the high magnification images of the sample yielded images of 60,000 or more red blood cells. FIG. 7 shows a schematic image 700 of a sample, acquired with blue illumination light (e.g., at a wavelength of 415 nm), although more generally, other illumination wavelengths (e.g., 635, 598, 525 nm) or combinations thereof can be used to acquire images, identify red blood cells, and determine cell volumes and constituent contents. Image 700 includes multiple identified objects 702A-J.

Figure 8:
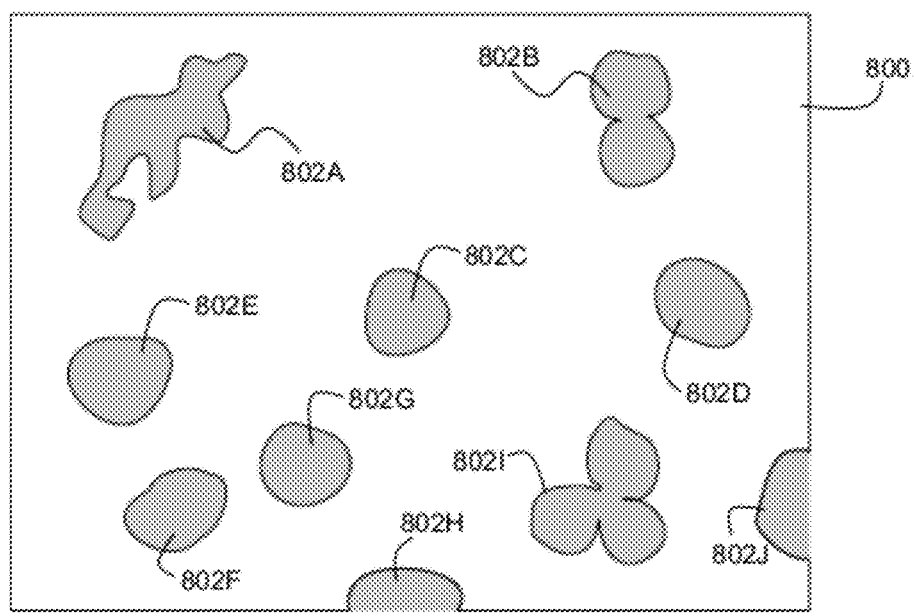
FIG. 8 is a schematic image of the blood sample of FIG. 7 after applying a threshold condition to the image.

Red blood cells were located within image 700 by applying a threshold condition to image 700. Specifically, only pixels having an intensity gray level of 160 or less (for an image at 8-bit resolution) were processed further, to exclude white blood cells from the red blood cell volume analysis. FIG. 8 is a schematic image 800 of the same sample that is shown in FIG. 7 after the threshold condition has been applied to the image. Objects 802A-J are present in image 800.

A connected components labeling process was then performed to correlate individual pixels in image 800 to objects 802A-J. After this process was complete, a pixel erosion mask was applied to each of the sets of pixels corresponding to objects 802A-J to remove the pixels representing the outermost 0.5 microns from the perimeter of each object. As disclosed above, the pixel erosion reduces image artifacts that are due to refraction of light from cell boundaries; these artifacts, if uncompensated, can lead to errors in cell volume determination.

Several features of each of objects 802A-J were measured, and the measurements are summarized in Table 1. The known area per pixel (0.022 square microns per pixel) was used to calculate an area for each of objects 802A-J. The area calculation included the entire area of the cell, including the portion of the area that was removed by the pixel erosion mask.

The roundness of objects 802A-J was also assessed by determining the deviation of the cross-sectional shape of each object from the profile of a perfect circle. As disclosed above, the ratio of the square of the perimeter to the area for a perfect circle is $4\pi$. The roundness column in Table 1 reflects the square-perimeter-to-area ratio for each object in image 800 divided by $4\pi$. A perfectly circular object will have a roundness value of 1, and the roundness value departs from 1 as the shape of the object becomes increasingly non-circular.

Optical density values were also measured for objects 802A-J. The gray level value for each pixel in each object was converted to an optical density value using Equation (2). The optical density values were determined for only the image pixels that were within the eroded mask. In turn, these optical density values were used to calculate a mean optical density and a maximum optical density value for each of the objects. In addition, integrated optical density values were calculated from the cell area and mean optical density values.

Objects 802A-J in FIG. 8 were each identified as possible red blood cells. Before calculating cell volumes, however, a representative set of red blood cells was selected from the group of objects 802A-J. To select representative red blood cells, the objects were evaluated with regard to their geometric and optical density properties to ensure they had suitable shapes and features corresponding to red blood cells.

In a first step, image 800 was scanned to determine whether any of the objects were cut off or otherwise obscured by the edge of the image (e.g., objects only partially contained within the image). Objects 802H and 802J were each cut-off by at the edge of image 800. Accordingly, objects 802H and 802J were excluded from further analysis; the results of this process are shown in Table 1 in the "Partial Cell" column.

The next step in the identification of the set of representative red blood cells was to determine whether the remaining objects (objects 802A-G and 802I) should be included in the set. To eliminate artifacts and/or groups of overlapping cells from the representative set, objects with an area larger than 65 square microns or an area smaller than 35 square microns were excluded from further analysis. In image 800, objects 802A, 802B, and 802I each had an area larger than 65 square microns (97, 76, and 103 square microns, respectively, as shown in Table 1). Accordingly, these objects were eliminated from the set of representative red blood cells. The shape of object 802A in FIG. 8 suggests this object corresponds to either a highly irregular single cell or to multiple cells. Objects 802B and 802I each appear to correspond to several clustered or overlapping cells.

The optical density values of the remaining objects 802C-G were then analyzed to determine whether these objects should be included in the set of representative red blood cells. In particular, a mean minimum optical density threshold value of 0.33 was applied to each object to exclude objects that corresponded to white blood cells. As shown in Table 1, object 800C had a mean optical density value of 0.29, which suggested that object 802C was not a red blood cell, but perhaps a white blood cell nucleus. A comparison of object 802C in image 800 and corresponding object 702C in image 700 suggested that object 802C corresponded to a white blood cell nucleus, and was therefore properly excluded from the representative set by application of the optical density threshold. Relative to image 700, the pixel intensity threshold removed contributions from the cytoplasm that were apparent in object 702C, leaving only the nucleus of the white blood cell visible in object 802C.

In addition, a mean maximum optical density threshold of 0.66 was applied to each of objects 802C-G to ensure that the objects did not correspond to multiple overlapping cells where the degree of overlap was sufficiently high such that the objects could not be rejected on the basis of shape irregularity. The optical density value for object 802F exceeded the threshold, and object 802F was therefore excluded from the set of representative red blood cells. A comparison of object 802F in FIG. 8 and corresponding object 702F in FIG. 7 suggested that object 802F corresponded to two overlapping cells, and was therefore properly excluded.

As a result, the representative set of red blood cells was reduced to objects 802D, 802E, and 802G. These representative red blood cells were then used to calculate the mean cell volume for the blood sample. The area, $OD_{mean}$, and $OD_{max}$ values from Table 1 for each of these objects were used in Equation (5) to calculate the volume for each object. The results of these volume calculations are shown in the "Volume" column of Table 1. Applying a correction factor of 0.5 to these Volume values expressed the cell volumes in femtoliters as shown in the "Volume (fL)" column in Table 1. The individual volumes for each of these cells were then used to calculate a mean cell volume for the sample, which was 11.36 fL. The foregoing process can be repeated for a plurality of image locations on the sample (e.g., several hundred or more), yielding a mean cell volume calculation based on hundreds or thousands of representative red blood cells in the sample. In addition, the process described above can be repeated to calculate color-specific integrated optical density, IOD(c), and color-specific cell volume, Vol (c), values from images acquired at a plurality of illumination wavelengths. For example, using a total of four colors of illumination (635, 598, 525, and 415 nm), the color specific integrated optical density and cell volume values can be used with Equation 8 to calculate a mean cell volume for the sample.

TABLE 1

| Object | Partial Cell | Area | $OD_{mean}$ | IOD | Roundness | $OD_{max}$ | Volume | Volume (fL) |
|---|---|---|---|---|---|---|---|---|
| 802A | No | 97 | 0.73 | 70.81 | 1.31 | 1.34 | N/A | N/A |
| 802B | No | 76 | 0.42 | 31.92 | 1.05 | 0.52 | N/A | N/A |
| 802C | No | 41 | 0.29 | 11.89 | 1.01 | 0.34 | N/A | N/A |
| 802D | No | 45 | 0.43 | 19.43 | 1.01 | 0.53 | 23.31 | 11.66 |
| 802E | No | 51 | 0.39 | 19.89 | 1.02 | 0.56 | 23.13 | 11.56 |

TABLE 1-continued

| Object | Partial Cell | Area | $OD_{mean}$ | IOD | Roundness | $OD_{max}$ | Volume | Volume (fL) |
|---|---|---|---|---|---|---|---|---|
| 802F | No | 47 | 0.53 | 24.91 | 1.03 | 0.84 | N/A | N/A |
| 802G | No | 42 | 0.44 | 18.48 | 1.01 | 0.55 | 21.74 | 10.87 |
| 802H | Yes | N/A | N/A | N/A | N/A | N/A | N/A | N/A |
| 802I | No | 103 | 0.41 | 42.23 | 1.04 | 0.51 | N/A | N/A |

Example 2

Table 2 illustrates an example implementation of Equation (11) to calculate mean cell hemoglobin values for blood samples based, in part, on a set of known MCH values for such samples. Six blood samples were processed using a known reference system, a calibrated automated hematology system using fluorescent flow cytometry methods to calculate the various parameters of a complete blood count including MCH. The "Reference MCH" column in Table 2 reports the mean cell hemoglobin value in picograms for each sample processed using this reference system.

The six samples were then processed and imaged, including the identification of sets of representative red blood cells for each sample, in the same manner as described above. For each sample, the system calculated an integrated optical density value for each color of illumination used to acquire images of the sample (i.e., yellow—635 nm; green—598 nm, and blue—415 nm). The integrated optical density values for each sample based on images obtained using the yellow, green, and blue light are reported in the Table 2 columns marked IOD(y), IOD(g), and IOD(b), respectively.

For each sample, three optical density values corresponding to the sample illumination colors were used to calculate a preliminary cell hemoglobin value. Weight coefficients previously determined from reference samples for each illumination wavelength were used in the following version of Equation (8):

$$H = -0.16 \cdot IOD(y) + 0.04 \cdot IOD(g) + 2.1 \cdot IOD(b)$$

Preliminary cell hemoglobin values for each sample are reported in the "H" column of Table 2. The preliminary cell hemoglobin values for each sample were then scaled to the corresponding mean cell hemoglobin values determined using the reference system. This scaling process included performing a regression analysis to correlate the preliminary cell hemoglobin values to the reported reference mean cell hemoglobin values for each sample. The optimal correlation corresponded to scaling the yellow weighting factor and adding an intercept value to the equation above that was used to calculate the preliminary cell hemoglobin measurements, as follows:

$$H = -0.17 \cdot IOD(y) + 0.04 \cdot IOD(g) + 2.1 \cdot IOD(b) + 0.5$$

Utilizing the foregoing equation, mean cell hemoglobin values were calculated for each sample, and are reported in the "Experimental MCH" column in Table 2. This equation could then be applied to new samples processed on the experimental system to calculate MCH values, without processing such samples on the reference system.

TABLE 2

| | IOD(y) | IOD(g) | IOD(b) | Reference MCH | H | Experimental MCH |
|---|---|---|---|---|---|---|
| Sample 1 | 7.73882 | 17.5825 | 13.1197 | 27.5 | 27.01646 | 27.43907 |
| Sample 2 | 7.78053 | 18.2845 | 15.3606 | 32.2 | 31.74376 | 32.16595 |
| Sample 3 | 7.2244 | 16.9506 | 14.8361 | 31.1 | 30.67793 | 31.10569 |
| Sample 4 | 6.88931 | 15.4531 | 14.4238 | 30.2 | 29.80581 | 30.23692 |
| Sample 5 | 8.624 | 17.846 | 15.7571 | 32.8 | 32.42391 | 32.83767 |
| Sample 6 | 6.93862 | 15.4893 | 13.0128 | 27.2 | 26.83627 | 27.26689 |

What is claimed is:

1. A method of determining a volume of a platelet, the method comprising:
   (a) illuminating the platelet with incident light at a plurality of illumination wavelengths;
   (b) obtaining at least one two-dimensional image of the platelet corresponding to each illumination wavelength;
   (c) for each illumination wavelength, determining a mean optical density and a maximum optical density for the platelet;
   (d) determining an area of the platelet;
   (e) for each illumination wavelength, determining a volume of the platelet based on the area of the platelet and the mean optical density and maximum optical density for the platelet corresponding to the illumination wavelength;
   (f) for each illumination wavelength, determining an integrated optical density for the platelet based on the area of the platelet and the mean optical density for the platelet corresponding to the illumination wavelength; and
   (g) determining the volume of the platelet based on a weighted combination of the area of the platelet, the volumes of the platelet corresponding to each of the illumination wavelengths, and the integrated optical densities for the platelet corresponding to each of the illumination wavelengths.

2. The method of claim 1, further comprising determining the volume of the platelet at each illumination wavelength based on a ratio of the mean optical density to the maximum optical density corresponding to the illumination wavelength.

3. The method of claim 1, wherein the plurality of illumination wavelengths comprises at least three illumination wavelengths.

4. The method of claim 1, wherein the plurality of illumination wavelengths comprises at least four illumination wavelengths.

5. The method of claim 1, further comprising determining the volume of the platelet at each illumination wavelength based on a ratio of the mean optical density to a sum of the maximum optical density and a correction factor at the illumination wavelength.

6. The method of claim 1, further comprising identifying a set of pixels in each image of the platelet that corresponds to the platelet.

7. The method of claim 1, further comprising:
   repeating steps (a) through (g) for a plurality of platelets from a sample of blood to determine volumes for each of the plurality of platelets; and
   determining a mean platelet volume for the sample from the volumes for each of the plurality of platelets.

8. The method of claim 3, wherein the plurality of illumination wavelengths comprises at least one wavelength between 575 nm and 600 nm, at least one wavelength between 525 nm and 570 nm, and at least one wavelength between 400 nm and 475 nm.

9. The method of claim 4, wherein the plurality of illumination wavelengths comprises at least one wavelength between 620 nm and 750 nm, at least one wavelength between 575 nm and 600 nm, at least one wavelength between 525 nm and 570 nm, and at least one wavelength between 400 nm and 475 nm.

10. The method of claim 5, further comprising adding an offset value to the ratio of the mean optical density to the sum of the maximum optical density and the correction factor to determine the volume of the platelet at each illumination wavelength.

11. The method of claim 10, further comprising determining values of the correction factor and the offset value from a reference set of blood samples.

12. The method of claim 6, wherein identifying the set of pixels comprises:
    identifying a first set of pixels that corresponds to a central region of the platelet;
    identifying a second set of pixels that corresponds to a non-central region of the platelet; and
    merging the first and second sets of pixels to form the set of pixels that corresponds to the platelet.

13. The method of claim 6, further comprising determining the area of the platelet based on the set of pixels.

14. The method of claim 12, further comprising identifying the second set of pixels based on intensity values for each member of the set of pixels in at least two images corresponding to different illumination wavelengths.

15. The method of claim 7, wherein the plurality of illumination wavelengths comprises an illumination wavelength in a blue region of the electromagnetic spectrum and an illumination wavelength in a yellow region of the electromagnetic spectrum, and the method comprises, for each respective platelet of the plurality of platelets, obtaining an image of the respective platelet corresponding to the illumination wavelength in the blue region and an image of the respective platelet corresponding to the illumination wavelength in the yellow region.

16. A method of assessing an operating condition of an automated blood analysis device, the method comprising:
    operating the device so that the device uses the method of claim 7 to determine a mean platelet volume for a control composition; and
    comparing a reference value of the mean platelet volume for the control composition to the determined value of the mean platelet volume to assess the operating condition of the device.

17. The method of claim 15, further comprising, for each respective platelet, excluding the respective platelet from the determination of the mean platelet volume if an integrated optical density for the respective platelet in the image corresponding to the illumination wavelength in the yellow region is larger than 600.

18. The method of claim 15, further comprising, for each respective platelet, excluding the respective platelet from the determination of the mean platelet volume if an integrated optical density for the respective platelet in the image corresponding to the illumination wavelength in the blue region is larger than 200.

19. The method of claim 16, further comprising:
    determining a difference between the determined and reference values of the mean platelet volume for the control composition; and
    re-calibrating the device if the difference exceeds a threshold value.

20. The method of claim 19, wherein re-calibrating the device comprises determining, from a reference set of blood samples, a plurality of weight coefficients that are used to determine the mean platelet volume for the sample based on the areas of the plurality of platelets, the volumes of the plurality of platelets corresponding to each of the illumination wavelengths, and the integrated optical densities for the plurality of platelets corresponding to each of the illumination wavelengths.

21. A system for determining a volume of a platelet, the system comprising:
an illumination source configured to illuminate the platelet with incident light at a plurality of illumination wavelengths;
a detector configured to obtain at least one two-dimensional image of the platelet corresponding to each illumination wavelength; and
an electronic processor configured to:
(a) determine a mean optical density and a maximum optical density for the platelet at each illumination wavelength;
(b) determine an area of the platelet;
(c) for each illumination wavelength, determine a volume of the platelet based on the area of the platelet and the mean optical density and maximum optical density for the platelet corresponding to the illumination wavelength;
(d) for each illumination wavelength, determine an integrated optical density for the platelet based on the area of the platelet and the mean optical density for the platelet corresponding to the illumination wavelength; and
(e) determine the volume of the platelet based on a weighted combination of the area of the platelet, the volumes of the platelet corresponding to each of the illumination wavelengths, and the integrated optical densities for the platelet corresponding to each of the illumination wavelengths.

22. The system of claim 21, wherein the plurality of illumination wavelengths comprises at least one wavelength between 575 nm and 600 nm, at least one wavelength between 525 nm and 570 nm, and at least one wavelength between 400 nm and 475 nm.

23. The system of claim 21, further comprising an automated blood sample preparation system.

24. The system of claim 21, wherein the plurality of illumination wavelengths comprises at least three illumination wavelengths.

25. The system of claim 21, wherein the plurality of illumination wavelengths comprises at least four illumination wavelengths.

26. The system of claim 21, wherein the electronic processor is further configured to determine the volume of the platelet at each illumination wavelength based on a ratio of the mean optical density to the maximum optical density corresponding to the illumination wavelength.

27. The system of claim 21, wherein the electronic processor is further configured to identify a set of pixels in each image of the platelet that corresponds to the platelet.

28. The system of claim 21, wherein the electronic processor is further configured to:
repeat steps (a) through (e) for a plurality of platelets from a sample of blood to determine volumes for each of the plurality of platelets; and
determine a mean platelet volume for the sample from the volumes for each of the plurality of platelets.

29. The system of claim 25, wherein the plurality of illumination wavelengths comprises at least one wavelength between 620 nm and 750 nm, at least one wavelength between 575 nm and 600 nm, at least one wavelength between 525 nm and 570 nm, and at least one wavelength between 400 nm and 475 nm.

30. The system of claim 26, wherein the electronic processor is further configured to add an offset value to the ratio of the mean optical density to the sum of the maximum optical density and the correction factor to determine the volume of the platelet at each illumination wavelength.

31. The system of claim 30, wherein the electronic processor is further configured to determine values of the correction factor and the offset value from a reference set of blood samples.

32. The system of claim 27, wherein the electronic processor is further configured to:
identify a first set of pixels that corresponds to a central region of the platelet;
identify a second set of pixels that corresponds to a non-central region of the platelet; and
merge the first and second sets of pixels to form the set of pixels that corresponds to the platelet.

33. The system of claim 32, wherein the electronic processor is further configured to identify the second set of pixels based on intensity values for each member of the set of pixels in at least two images corresponding to different illumination wavelengths.

34. The system of claim 28, wherein the sample is a control composition, and wherein the electronic processor is further configured to:
determine a mean platelet volume for the control composition; and
compare a reference value of the mean platelet volume for the control composition to the determined value of the mean platelet volume to assess an operating condition of a device that comprises the system.

35. The system of claim 28, wherein the plurality of illumination wavelengths comprises an illumination wavelength in a blue region of the electromagnetic spectrum and an illumination wavelength in a yellow region of the electromagnetic spectrum, and the electronic processor is further configured to obtain, for each respective platelet of the plurality of platelets, an image of the respective platelet corresponding to the illumination wavelength in the blue region and an image of the respective platelet corresponding to the illumination wavelength in the yellow region.

36. The system of claim 34, wherein the electronic processor is further configured to:
determine a difference between the determined and reference values of the mean platelet volume for the control composition; and
re-calibrate the device if the difference exceeds a threshold value.

37. The system of claim 36, wherein the electronic processor is further configured to re-calibrate the device by determining, from a reference set of blood samples, a plurality of weight coefficients that are used to determine the mean platelet volume for the sample based on the areas of the plurality of platelets, the volumes of the plurality of platelets corresponding to each of the illumination wavelengths, and the integrated optical densities for the plurality of platelets corresponding to each of the illumination wavelengths.

38. The system of claim 35, wherein for each respective platelet, the electronic processor is further configured to exclude the respective platelet from the determination of the mean platelet volume if an integrated optical density for the respective platelet in the image corresponding to the illumination wavelength in the yellow region is larger than 600.

39. The system of claim 35, wherein for each respective platelet, the electronic processor is further configured to exclude the respective platelet from the determination of the mean platelet volume if an integrated optical density for the respective platelet in the image corresponding to the illumination wavelength in the blue region is larger than 200.

40. The system of claim 27, wherein the electronic processor is further configured to determine the area of the platelet based on the set of pixels.

* * * * *